(12) United States Patent
Lee et al.

(10) Patent No.: US 9,326,843 B2
(45) Date of Patent: May 3, 2016

(54) INTRAVASCULAR BLOOD FILTERS AND METHODS OF USE

(75) Inventors: Michael Lee, Santa Rosa, CA (US);
Daniel W. Fifer, Windsor, CA (US);
Randall T. Lashinski, Windsor, CA (US)

(73) Assignee: Claret Medical, Inc., Santa Rosa, CA (US)

( * ) Notice: Subject to any disclaimer, the term of this patent is extended or adjusted under 35 U.S.C. 154(b) by 481 days.

(21) Appl. No.: 12/871,708

(22) Filed: Aug. 30, 2010

(65) Prior Publication Data

US 2011/0282379 A1 Nov. 17, 2011

Related U.S. Application Data

(63) Continuation-in-part of application No. 12/689,997, filed on Jan. 19, 2010, now Pat. No. 8,372,108.

(60) Provisional application No. 61/145,149, filed on Jan. 16, 2009, provisional application No. 61/244,418, filed on Sep. 21, 2009, provisional application No. 61/334,893, filed on May 14, 2010, provisional application No. 61/348,979, filed on May 27, 2010.

(51) Int. Cl.
*A61M 29/00* (2006.01)
*A61F 2/01* (2006.01)
*A61M 25/01* (2006.01)

(52) U.S. Cl.
CPC . *A61F 2/01* (2013.01); *A61F 2/013* (2013.01); *A61F 2002/018* (2013.01);
(Continued)

(58) Field of Classification Search
CPC ............... A61B 1/0049; A61B 1/0081; A61B 2017/2908; A61B 1/0055; A61B 1/0056; A61B 1/0057; A61B 2017/003; A61B 2017/00305; A61B 2017/00309; A61B 2017/00314; A61B 2017/00323; A61F 2/013; A61F 2002/018; A61F 2250/0029; A61M 2025/0161; A61M 25/0147; A61M 25/0138; A61M 25/0133; A61M 25/0141; A61M 25/0144; A61M 25/0152; A61M 25/005; A61M 25/0051; A61M 25/0052; A61M 25/0053; A61M 25/0054; A61M 25/0013; A61M 25/0012; A61M 2025/0152
USPC ............ 606/200; 600/146, 149; 604/534, 525
See application file for complete search history.

(56) References Cited

U.S. PATENT DOCUMENTS

| 3,472,230 A | 10/1969 | Fogarty |
| 4,619,246 A | 10/1986 | Molgaard-Nielsen et al. |

(Continued)

FOREIGN PATENT DOCUMENTS

| DE | 10049812 | 4/2002 |
| EP | 1400257 A2 | 3/2004 |

(Continued)

OTHER PUBLICATIONS

International Search Report in Application No. PCT/US2010/043390 dated Apr. 8, 2011, in 11 pages.

(Continued)

*Primary Examiner* — David C Eastwood
*Assistant Examiner* — Martin T Ton
(74) *Attorney, Agent, or Firm* — Knobbe Martens Olson & Bear LLP

(57) ABSTRACT

Multi-filter endolumenal methods and systems for filtering fluids within the body. In some embodiments a multi-filter blood filtering system captures and removes particulates dislodge or generated during a surgical procedure and circulating in a patient's vasculature. In some embodiments a dual filter system protects the cerebral vasculature during a cardiac valve repair or replacement procedure.

48 Claims, 37 Drawing Sheets

(52) U.S. Cl.
CPC .. *A61F 2230/0006* (2013.01); *A61F 2230/008* (2013.01); *A61F 2230/0008* (2013.01); *A61F 2230/0067* (2013.01); *A61M 25/0133* (2013.01); *A61M 25/0147* (2013.01); *A61M 2025/0161* (2013.01)

(56) References Cited

U.S. PATENT DOCUMENTS

| | | | |
|---|---|---|---|
| 4,630,609 A | 12/1986 | Chin | |
| 4,650,466 A | 3/1987 | Luther | |
| 4,706,671 A | 11/1987 | Weinrib | |
| 4,723,549 A | 2/1988 | Wholey et al. | |
| 4,873,978 A | 10/1989 | Ginsburg | |
| 5,108,419 A | 4/1992 | Reger | |
| 5,192,286 A | 3/1993 | Phan | |
| 5,329,923 A * | 7/1994 | Lundquist | 600/373 |
| 5,348,545 A | 9/1994 | Shani et al. | |
| 5,381,782 A | 1/1995 | DeLaRama et al. | |
| 5,395,327 A | 3/1995 | Lundquist et al. | |
| 5,613,980 A | 3/1997 | Chauhan | |
| 5,624,430 A | 4/1997 | Eton et al. | |
| 5,662,671 A | 9/1997 | Barbut et al. | |
| 5,707,389 A | 1/1998 | Louw et al. | |
| 5,766,151 A | 6/1998 | Valley et al. | |
| 5,779,716 A | 7/1998 | Cano et al. | |
| 5,814,064 A | 9/1998 | Daniel | |
| 5,827,324 A | 10/1998 | Cassell | |
| 5,833,650 A | 11/1998 | Imran | |
| 5,848,964 A | 12/1998 | Samuels | |
| 5,897,529 A | 4/1999 | Ponzi | |
| 5,897,819 A | 4/1999 | Miyata et al. | |
| 5,910,154 A | 6/1999 | Tsugita et al. | |
| 5,910,364 A | 6/1999 | Miyata et al. | |
| 5,911,734 A | 6/1999 | Tsugita et al. | |
| 5,935,139 A | 8/1999 | Bates | |
| 5,980,555 A | 11/1999 | Barbut et al. | |
| 5,989,281 A * | 11/1999 | Barbut et al. | 606/200 |
| 5,993,469 A | 11/1999 | McKenzie et al. | |
| 6,001,118 A | 12/1999 | Daniel | |
| 6,010,522 A | 1/2000 | Barbut et al. | |
| 6,027,520 A | 2/2000 | Tsugita et al. | |
| 6,042,598 A | 3/2000 | Tsugita et al. | |
| 6,045,547 A | 4/2000 | Ren et al. | |
| 6,080,140 A | 6/2000 | Swaminathan et al. | |
| 6,083,239 A | 7/2000 | Addis | |
| 6,096,053 A | 8/2000 | Bates | |
| 6,099,534 A | 8/2000 | Bates | |
| 6,120,494 A | 9/2000 | Jonkman | |
| 6,142,987 A | 11/2000 | Tsugita | |
| 6,152,946 A | 11/2000 | Broome et al. | |
| 6,171,328 B1 | 1/2001 | Addis | |
| 6,179,851 B1 | 1/2001 | Barbut et al. | |
| 6,235,045 B1 | 5/2001 | Barbut et al. | |
| 6,245,087 B1 | 6/2001 | Addis | |
| 6,245,088 B1 | 6/2001 | Lowery | |
| 6,245,089 B1 | 6/2001 | Daniel | |
| 6,264,663 B1 | 7/2001 | Cano | |
| 6,270,513 B1 | 8/2001 | Tsugita et al. | |
| 6,277,138 B1 | 8/2001 | Levinson et al. | |
| 6,290,710 B1 | 9/2001 | Cryer et al. | |
| 6,309,399 B1 | 10/2001 | Barbut et al. | |
| 6,325,815 B1 | 12/2001 | Kusleika et al. | |
| 6,336,934 B1 | 1/2002 | Gilson et al. | |
| 6,346,116 B1 | 2/2002 | Brooks et al. | |
| 6,361,545 B1 | 3/2002 | Macoviak et al. | |
| 6,364,900 B1 | 4/2002 | Heuser | |
| 6,371,971 B1 | 4/2002 | Tsugita et al. | |
| 6,383,174 B1 | 5/2002 | Eder | |
| 6,383,205 B1 | 5/2002 | Samson et al. | |
| 6,440,120 B1 | 8/2002 | Maahs | |
| 6,485,502 B2 | 11/2002 | Don Michael et al. | |
| 6,517,559 B1 | 2/2003 | O'Connell | |
| 6,558,356 B2 | 5/2003 | Barbut | |
| 6,595,983 B2 | 7/2003 | Voda | |
| 6,605,102 B1 | 8/2003 | Mazzocchi et al. | |
| 6,620,148 B1 | 9/2003 | Tsugita | |
| 6,648,837 B2 | 11/2003 | Kato et al. | |
| 6,663,652 B2 | 12/2003 | Daniel et al. | |
| 6,676,682 B1 | 1/2004 | Tsugita et al. | |
| 6,712,834 B2 * | 3/2004 | Yassour et al. | 606/200 |
| 6,712,835 B2 | 3/2004 | Mazzocchi | |
| 6,726,651 B1 | 4/2004 | Robinson et al. | |
| 6,726,701 B2 | 4/2004 | Gilson et al. | |
| 6,740,061 B1 | 5/2004 | Oslund et al. | |
| 6,817,999 B2 | 11/2004 | Berube et al. | |
| 6,830,579 B2 | 12/2004 | Barbut | |
| 6,843,798 B2 | 1/2005 | Kusleika et al. | |
| 6,872,216 B2 | 3/2005 | Daniel | |
| 6,881,194 B2 | 4/2005 | Miyata et al. | |
| 6,887,258 B2 | 5/2005 | Denison et al. | |
| 6,905,490 B2 | 6/2005 | Parodi | |
| 6,907,298 B2 | 6/2005 | Smits et al. | |
| 6,969,396 B2 | 11/2005 | Krolik et al. | |
| 7,011,094 B2 | 3/2006 | Rapacki et al. | |
| 7,048,752 B2 | 5/2006 | Mazzocchi | |
| 7,094,249 B1 | 8/2006 | Broome et al. | |
| 7,115,134 B2 | 10/2006 | Chambers | |
| 7,160,255 B2 | 1/2007 | Saadat | |
| 7,169,161 B2 | 1/2007 | Bonnette et al. | |
| 7,169,165 B2 | 1/2007 | Belef et al. | |
| 7,182,757 B2 | 2/2007 | Miyata et al. | |
| 7,214,237 B2 | 5/2007 | Don Michael et al. | |
| 7,278,974 B2 | 10/2007 | Kato et al. | |
| 7,313,445 B2 | 12/2007 | McVenes et al. | |
| 7,323,001 B2 | 1/2008 | Clubb et al. | |
| 7,399,308 B2 * | 7/2008 | Borillo et al. | 606/200 |
| 7,410,491 B2 | 8/2008 | Hopkins | |
| 7,493,154 B2 | 2/2009 | Bonner et al. | |
| 7,559,925 B2 | 7/2009 | Goldfarb et al. | |
| 7,572,272 B2 | 8/2009 | Denison et al. | |
| 7,621,904 B2 * | 11/2009 | McFerran et al. | 604/525 |
| 7,766,961 B2 | 8/2010 | Patel et al. | |
| 7,918,859 B2 | 4/2011 | Katoh et al. | |
| 7,922,732 B2 | 4/2011 | Mazzocchi et al. | |
| 7,998,104 B2 | 8/2011 | Chang | |
| 8,002,790 B2 | 8/2011 | Brady et al. | |
| 8,372,108 B2 | 2/2013 | Lashinski | |
| 8,382,788 B2 | 2/2013 | Galdonik | |
| 8,518,073 B2 | 8/2013 | Lashinski | |
| 8,753,370 B2 | 6/2014 | Lashinski | |
| 8,876,796 B2 | 11/2014 | Fifer et al. | |
| 8,974,489 B2 | 3/2015 | Lashinski | |
| 9,017,364 B2 | 4/2015 | Fifer et al. | |
| 9,055,997 B2 | 6/2015 | Fifer et al. | |
| 2001/0041858 A1 | 11/2001 | Ray et al. | |
| 2002/0026145 A1 | 2/2002 | Bagaoisan et al. | |
| 2002/0055767 A1 | 5/2002 | Forde et al. | |
| 2002/0077596 A1 | 6/2002 | McKenzie et al. | |
| 2002/0095170 A1 | 7/2002 | Krolik et al. | |
| 2002/0095172 A1 | 7/2002 | Mazzocchi et al. | |
| 2002/0123761 A1 | 9/2002 | Barbut et al. | |
| 2002/0161394 A1 | 10/2002 | Macoviak et al. | |
| 2002/0165571 A1 | 11/2002 | Hebert et al. | |
| 2003/0100919 A1 | 5/2003 | Hopkins et al. | |
| 2003/0130684 A1 | 7/2003 | Brady et al. | |
| 2003/0171770 A1 | 9/2003 | Kusleika et al. | |
| 2004/0002730 A1 | 1/2004 | Denison et al. | |
| 2004/0044350 A1 * | 3/2004 | Martin et al. | 606/139 |
| 2004/0044360 A1 | 3/2004 | Lowe | |
| 2004/0064092 A1 | 4/2004 | Tsugita et al. | |
| 2004/0093015 A1 | 5/2004 | Ogle | |
| 2004/0167565 A1 | 8/2004 | Beulke et al. | |
| 2004/0193206 A1 | 9/2004 | Gerberding | |
| 2004/0215167 A1 | 10/2004 | Belson | |
| 2004/0220611 A1 | 11/2004 | Ogle | |
| 2004/0225321 A1 | 11/2004 | Krolik et al. | |
| 2004/0230220 A1 | 11/2004 | Osborne | |
| 2004/0243175 A1 | 12/2004 | Don Michael | |
| 2004/0254601 A1 | 12/2004 | Eskuri | |
| 2004/0254602 A1 | 12/2004 | Lehe et al. | |
| 2005/0010285 A1 | 1/2005 | Lambrecht et al. | |
| 2005/0065397 A1 * | 3/2005 | Saadat et al. | 600/104 |
| 2005/0080356 A1 | 4/2005 | Dapolito et al. | |
| 2005/0101987 A1 | 5/2005 | Salahieh | |

(56) References Cited

U.S. PATENT DOCUMENTS

| | | |
|---|---|---|
| 2005/0131449 A1 | 6/2005 | Salahieh et al. |
| 2005/0137696 A1 | 6/2005 | Salahieh |
| 2005/0177132 A1* | 8/2005 | Lentz et al. ............... 604/525 |
| 2006/0015136 A1 | 1/2006 | Besselink |
| 2006/0015138 A1 | 1/2006 | Gertner |
| 2006/0030877 A1 | 2/2006 | Martinez et al. |
| 2006/0041188 A1 | 2/2006 | Dirusso et al. |
| 2006/0089666 A1 | 4/2006 | Linder et al. |
| 2006/0100658 A1* | 5/2006 | Obana et al. ............... 606/200 |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0149350 A1 | 7/2006 | Patel et al. |
| 2006/0161241 A1 | 7/2006 | Barbut et al. |
| 2006/0200191 A1 | 9/2006 | Zadno-Azizi |
| 2006/0259066 A1 | 11/2006 | Euteneuer |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0244504 A1 | 10/2007 | Keegan et al. |
| 2008/0004687 A1 | 1/2008 | Barbut et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0125848 A1 | 5/2008 | Kusleika et al. |
| 2008/0154153 A1 | 6/2008 | Heuser |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1* | 11/2009 | Legaspi et al. ............... 604/523 |
| 2009/0326575 A1 | 12/2009 | Galdonik et al. |
| 2010/0004633 A1 | 1/2010 | Rothe et al. |
| 2010/0063537 A1 | 3/2010 | Ren et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0185231 A1 | 7/2010 | Lashinski |
| 2010/0191276 A1 | 7/2010 | Lashinski |
| 2010/0211095 A1 | 8/2010 | Carpenter |
| 2010/0312268 A1 | 12/2010 | Belson |
| 2010/0324589 A1 | 12/2010 | Carpenter et al. |
| 2011/0022076 A1 | 1/2011 | Lashinski |
| 2011/0066221 A1 | 3/2011 | White et al. |
| 2011/0282379 A1 | 11/2011 | Lee et al. |
| 2012/0046739 A1 | 2/2012 | von Oepen et al. |
| 2012/0095500 A1 | 4/2012 | Heuser |
| 2012/0172915 A1 | 7/2012 | Fifer et al. |
| 2012/0172916 A1 | 7/2012 | Fifer et al. |
| 2012/0172917 A1 | 7/2012 | Fifer et al. |
| 2012/0172919 A1 | 7/2012 | Fifer et al. |
| 2012/0203265 A1 | 8/2012 | Heuser |
| 2012/0289996 A1 | 11/2012 | Lee et al. |
| 2013/0131714 A1 | 5/2013 | Wang et al. |
| 2013/0231694 A1 | 9/2013 | Lashinski |
| 2014/0052170 A1 | 2/2014 | Heuser et al. |
| 2014/0094843 A1 | 4/2014 | Heuser |
| 2014/0243877 A9 | 8/2014 | Lee et al. |
| 2014/0282379 A1 | 9/2014 | Lee et al. |
| 2015/0039016 A1 | 2/2015 | Naor et al. |
| 2015/0209131 A1 | 7/2015 | Fifer et al. |
| 2015/0230910 A1 | 8/2015 | Lashinski et al. |

FOREIGN PATENT DOCUMENTS

| | | |
|---|---|---|
| EP | 1253871 | 2/2007 |
| EP | 2303384 | 4/2011 |
| EP | 2391303 | 12/2011 |
| EP | 2480165 | 8/2012 |
| EP | 2658476 | 11/2013 |
| EP | 2387427 | 8/2014 |
| JP | 2011-525405 A | 9/2011 |
| WO | WO 99/23976 A1 | 5/1999 |
| WO | WO 2004/026175 | 4/2004 |
| WO | WO 2008/100790 A2 | 8/2008 |
| WO | WO 2008/113857 | 9/2008 |
| WO | WO 2010/008451 | 1/2010 |
| WO | WO 2010/083527 | 7/2010 |
| WO | WO 2010/088520 | 8/2010 |
| WO | WO 2011/034718 | 3/2011 |
| WO | WO 2011/017103 | 10/2011 |
| WO | PCT/US2011/067598 | 12/2011 |

OTHER PUBLICATIONS

International Search Report in Application No. PCT/US2011/067598 dated May 10, 2012, in 45 pages.

International Preliminary of Patentability in Application No. PCT/US2010/022590 dated Jan. 29, 2010, in 4 pages.

Lashinski, Randall; U.S. Appl. No. 12/844,420 emtititled "Dual Endovascular Filter and Methods of Use," filed Jul. 27, 2010.

International Search Report in Application No. PCT/US2010/021417 dated Aug. 23, 2010, in 4 pages.

International Search Report in Application No. PCT/US2010/047166 dated Apr. 27, 2011, in 7 pages.

Supplementary European Search Report in Application No. PCT/US2010/021417 dated Nov. 28, 2012, in 5 pages.

Supplementary European Search Report in Application No. PCT/US2010/047166 dated Feb. 20, 2013, in 6 pages.

Notice of Allowance for U.S. Appl. No. 12/689,997 dated Jan. 9, 2013, in 9 pages.

Office Action for U.S. Appl. 13/497,235 dated Apr. 2, 2015, in 21 pages.

Office Action for U.S. Appl. No. 13/738,847 dated Apr. 29, 2015, in 16 pages.

* cited by examiner

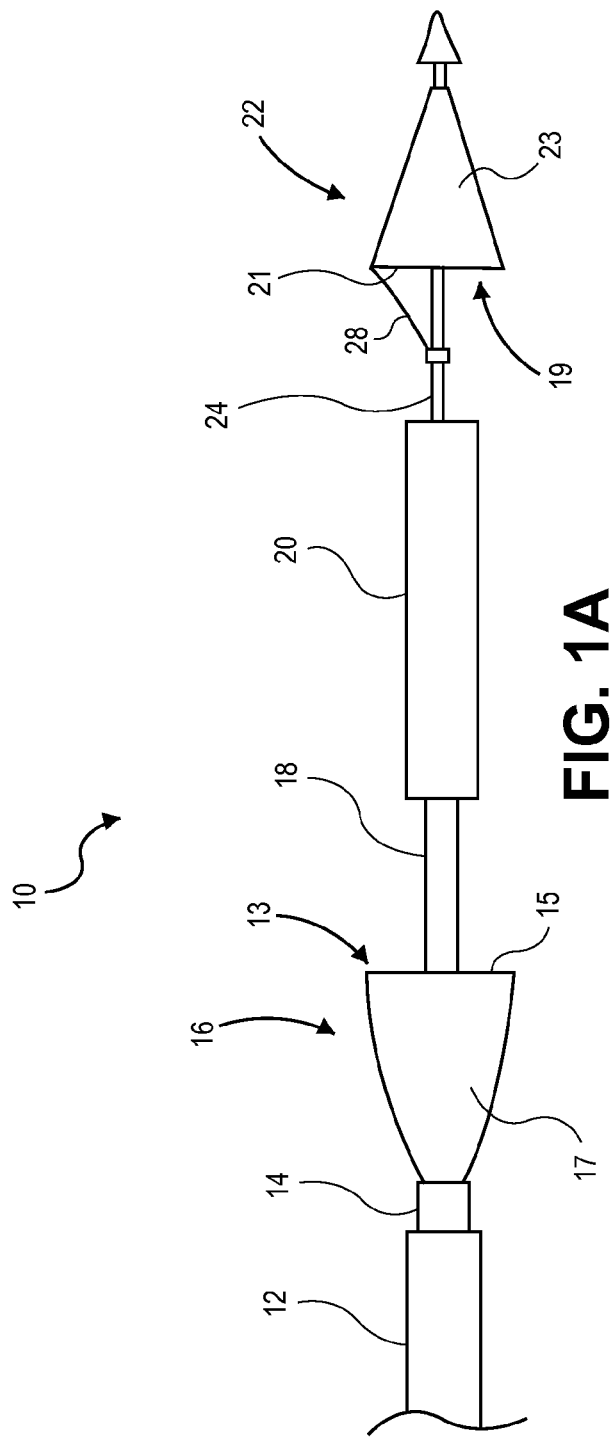
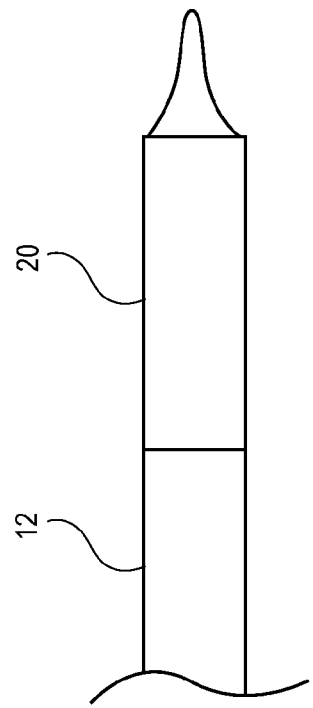
FIG. 1A
FIG. 1B

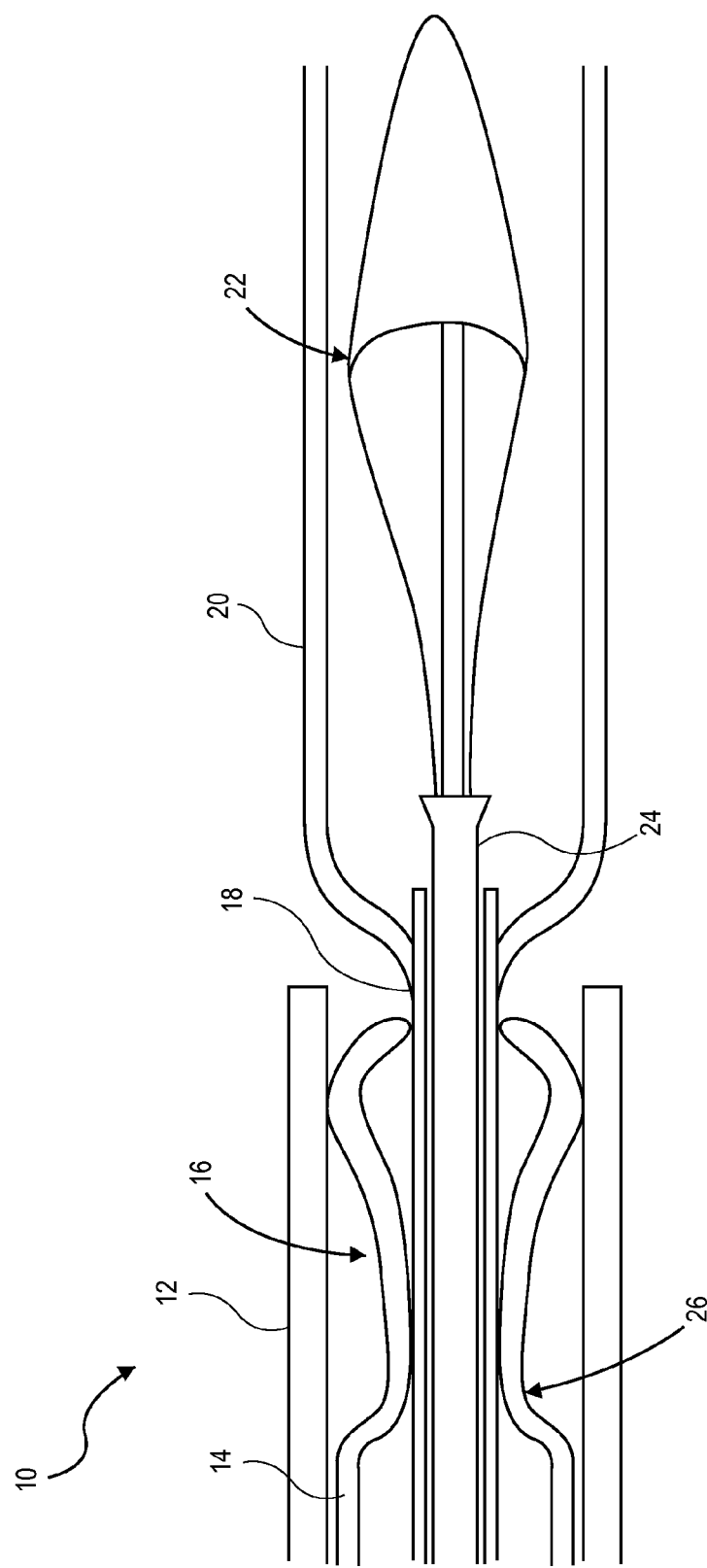

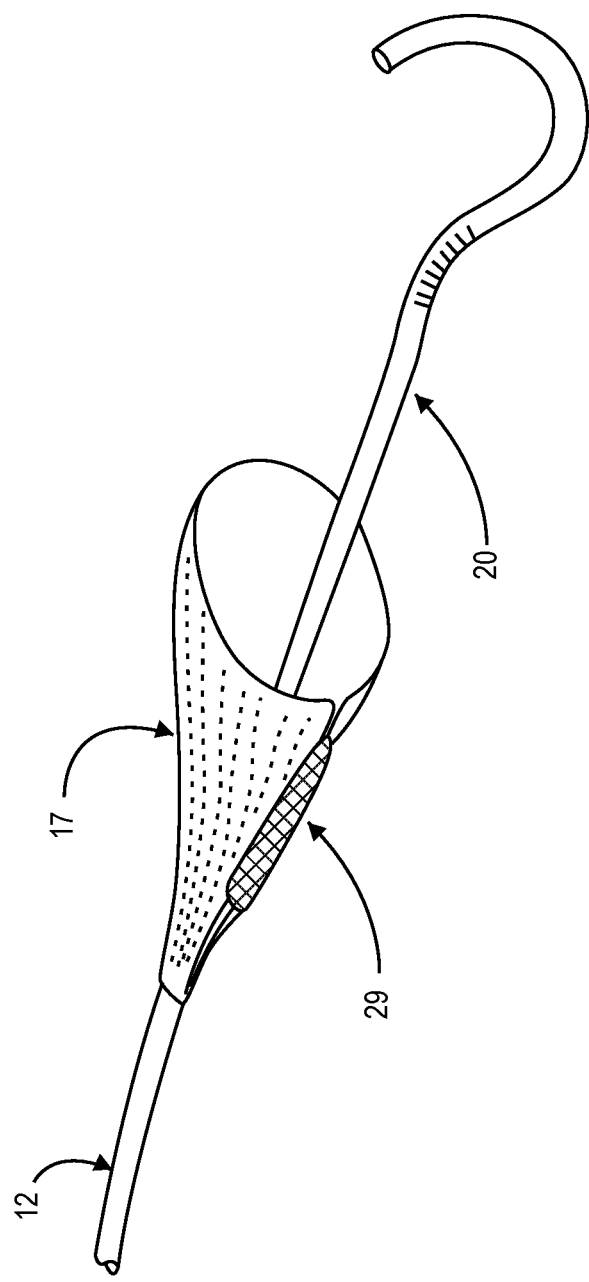

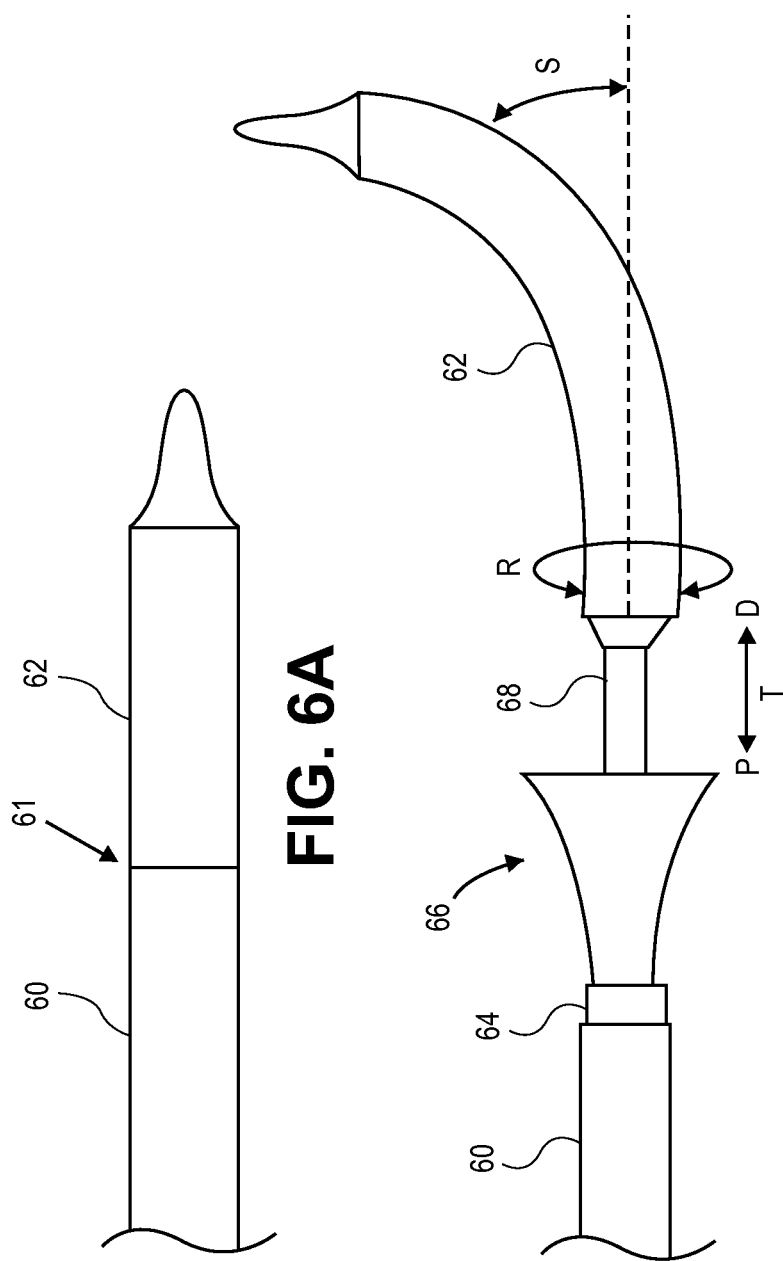

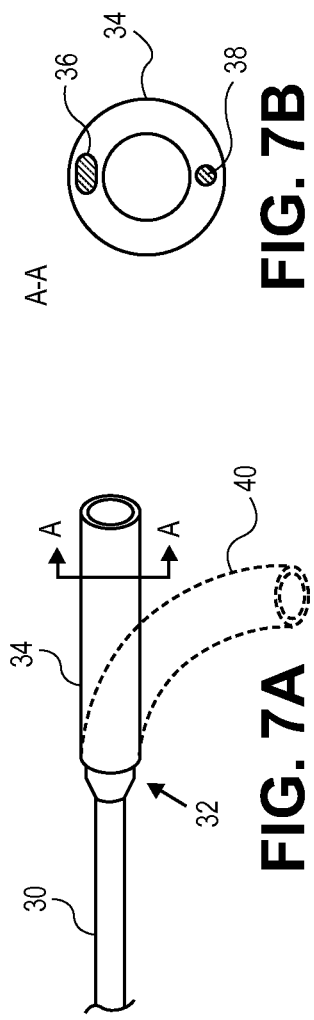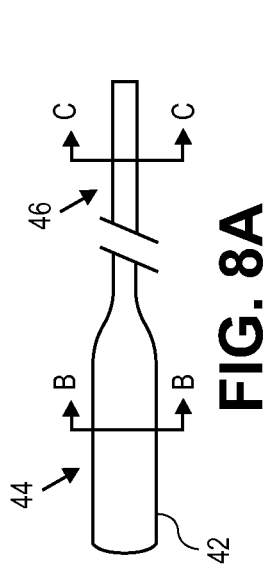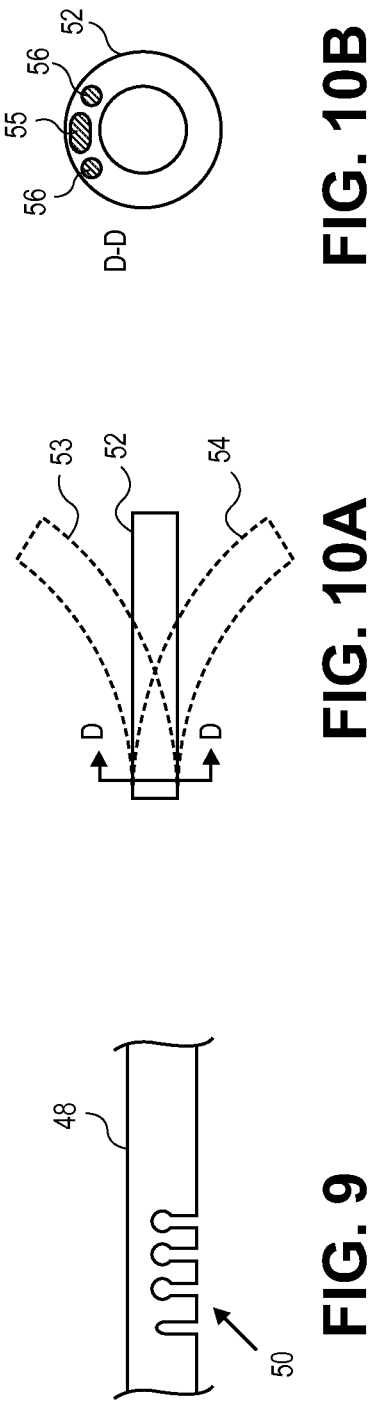

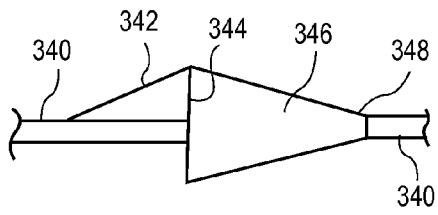
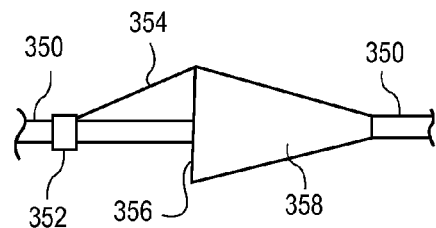
FIG. 23A    FIG. 23B
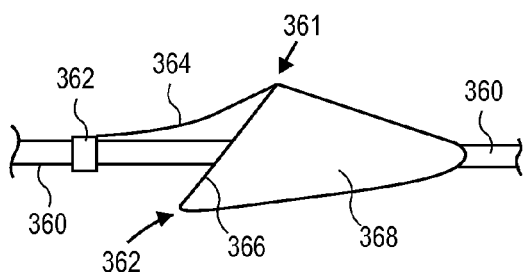
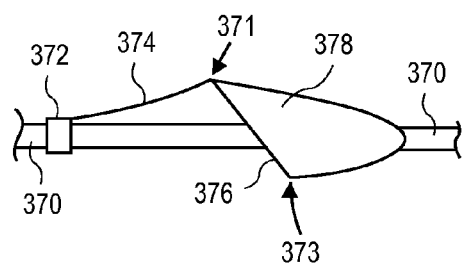
FIG. 23C    FIG. 23D
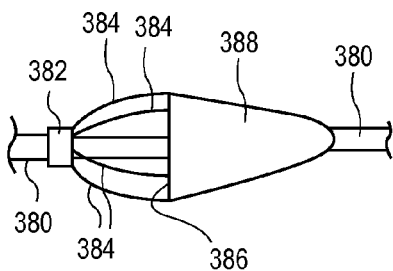
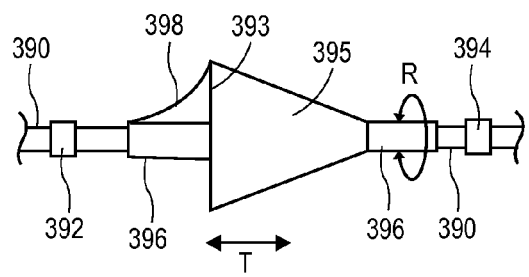
FIG. 23E    FIG. 23F
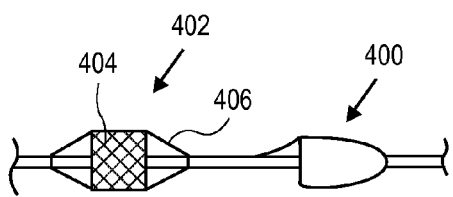
FIG. 24A
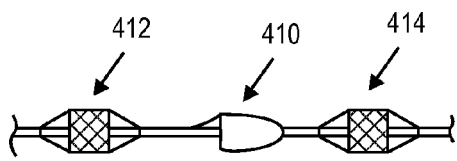
FIG. 24B
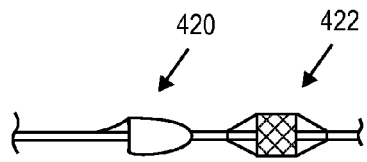
FIG. 24C

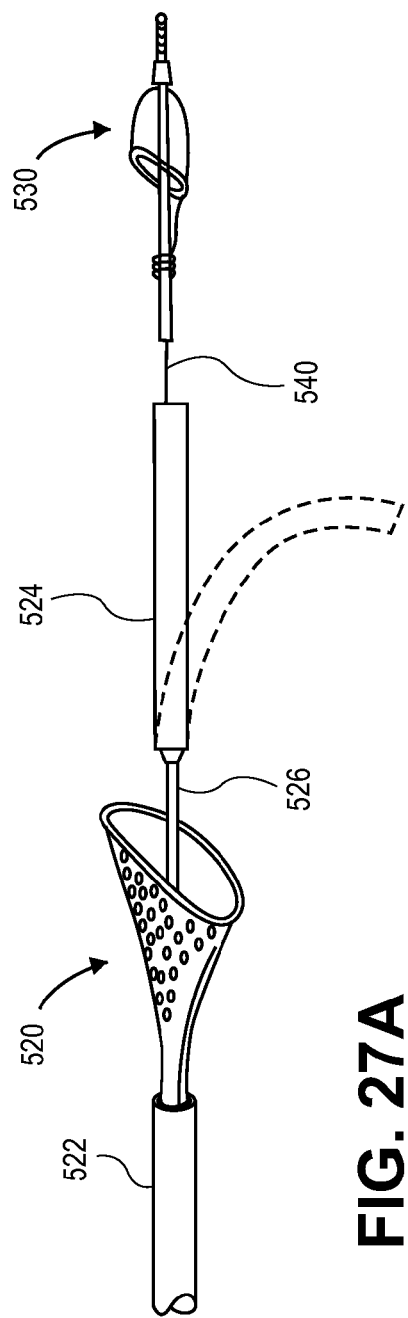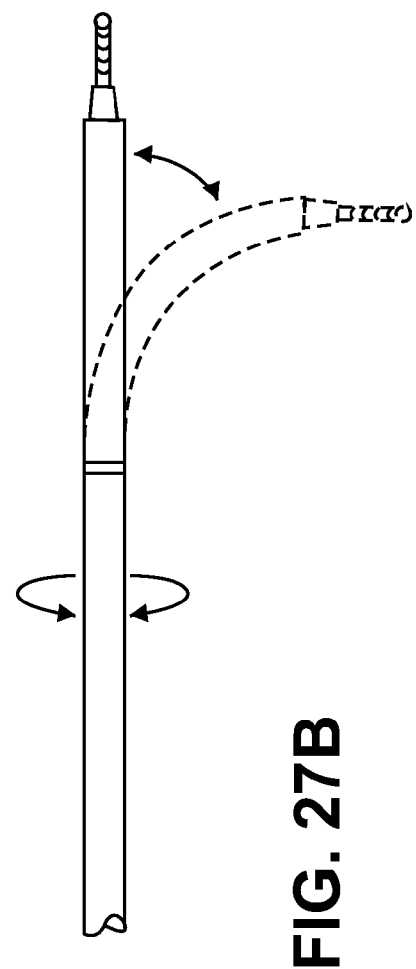
FIG. 27A
FIG. 27B

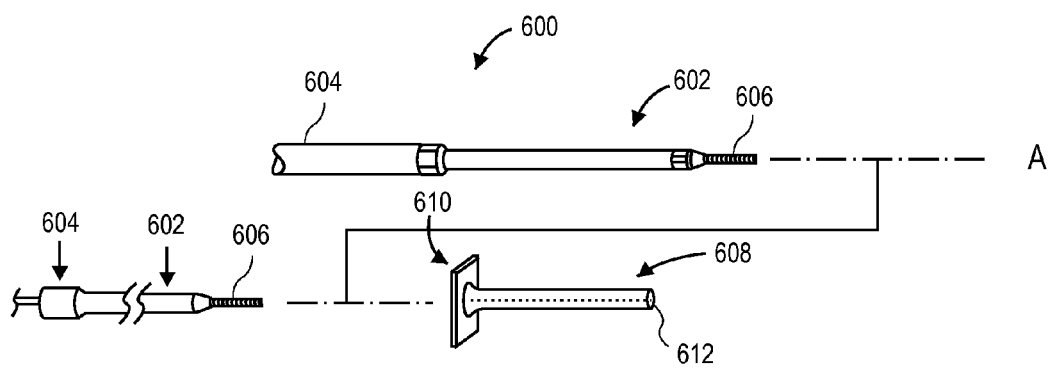
FIG. 29A
FIG. 29B
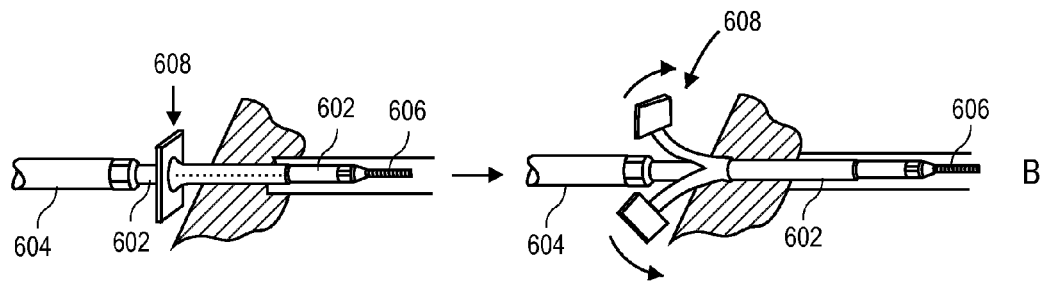
FIG. 29C
FIG. 29D
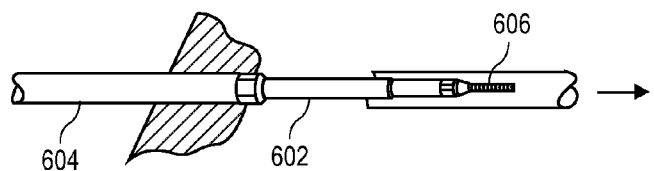
FIG. 29E

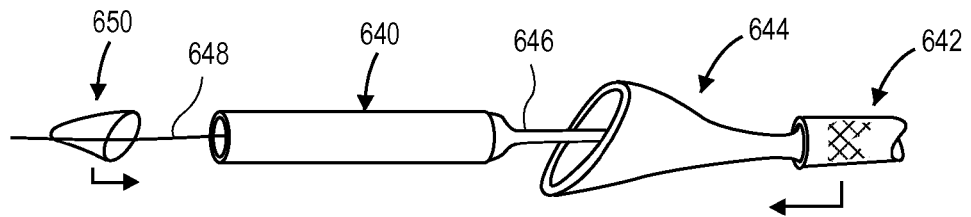
FIG. 30A
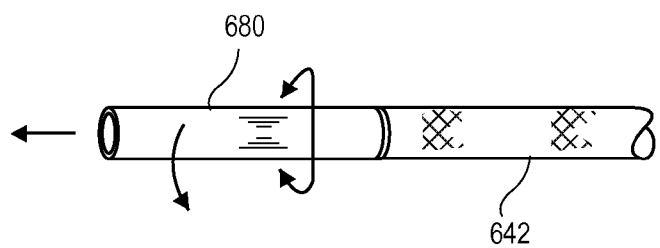
FIG. 30B
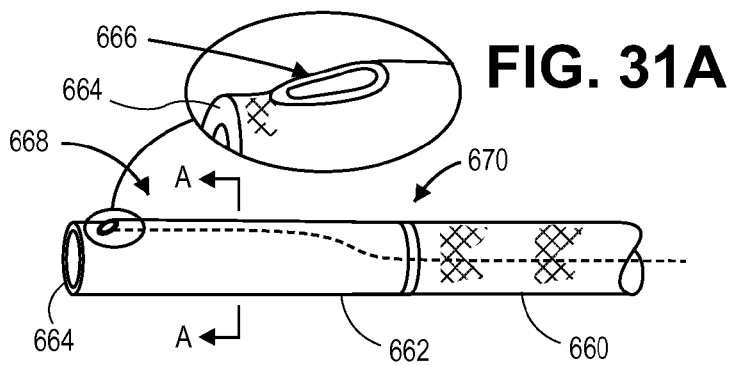
FIG. 31A
FIG. 31B
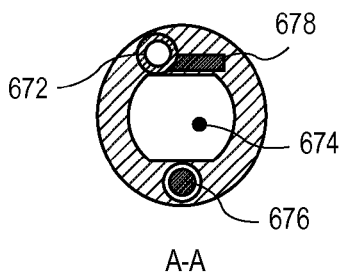
FIG. 31C

INTRAVASCULAR BLOOD FILTERS AND METHODS OF USE

CROSS-REFERENCE TO RELATED APPLICATIONS

This application is a continuation-in-part of U.S. application Ser. No. 12/689,997, filed Jan. 19, 2010, now U.S. Pat. No. 8,372,108 which claims the benefit of U.S. Provisional Patent Application No. 61/145,149, filed Jan. 16, 2009, both of which are incorporated herein by reference. This application also claims the benefit of U.S. Provisional Application No. 61/244,418, filed Sep. 21, 2009; U.S. Provisional Application No. 61/334,893, filed May 14, 2010; and U.S. Provisional Application No. 61/348,979, filed May 27, 2010, all of which are incorporated herein by reference.

BACKGROUND OF THE INVENTION

Thromboembolic disorders, such as stroke, pulmonary embolism, peripheral thrombosis, atherosclerosis, and the like, affect many people. These disorders are a major cause of morbidity and mortality in the United States and throughout the world. Thromboembolic events are characterized by an occlusion of a blood vessel. The occlusion can be caused by a clot which is viscoelastic (jelly-like) and is comprised of platelets, fibrinogen, and other clotting proteins.

Percutaneous aortic valve replacement has been in development for some time now and stroke rates related to this procedure are between four and twenty percent. During catheter delivery and valve implantation plaque may be dislodged from the vasculature and may travel through the carotid circulation and into the brain. When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

Techniques exist to reestablish blood flow in an occluded vessel. One common surgical technique, an embolectomy, involves incising a blood vessel and introducing a balloon-tipped device (such as a Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and is best avoided when possible. Additionally, the use of a Fogarty catheter may be problematic due to the possible risk of damaging the interior lining of the vessel as the catheter is being withdrawn.

A common percutaneous technique is referred to as balloon angioplasty where a balloon-tipped catheter is introduced into a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse Streptokinase, Urokinase, or other thrombolytic agents to dissolve the clot. Unfortunately, thrombolysis typically takes hours or days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. Retrieval devices exist for the removal of foreign bodies, some of which form a loop that can ensnare the foreign material by decreasing the size of the diameter of the loop around the foreign body. The use of such removal devices can be difficult and sometimes unsuccessful.

Moreover, systems heretofore disclosed in the art are generally limited by size compatibility and the increase in vessel size as the emboli is drawn out from the distal vascular occlusion location to a more proximal location near the heart. If the embolectomy device is too large for the vessel it will not deploy correctly to capture the clot or foreign body, and if too small in diameter it cannot capture clots or foreign bodies across the entire cross section of the blood vessel. Additionally, if the embolectomy device is too small in retaining volume then as the device is retracted the excess material being removed can spill out and be carried by flow back to occlude another vessel downstream.

Various thrombectomy and foreign matter removal devices have been disclosed in the art. Such devices, however, have been found to have structures which are either highly complex or lacking in sufficient retaining structure. Disadvantages associated with the devices having highly complex structure include difficulty in manufacturability as well as difficulty in use in conjunction with microcatheters. Recent developments in the removal device art features umbrella filter devices having self folding capabilities. Typically, these filters fold into a pleated condition, where the pleats extend radially and can obstruct retraction of the device into the microcatheter sheathing.

Extraction systems are needed that can be easily and controllably deployed into and retracted from the circulatory system for the effective removal of clots and foreign bodies. There is also a need for systems that can be used as temporary arterial or venous filters to capture and remove thromboemboli generated during endovascular procedures. The systems should also be able to be properly positioned in the desired location. Additionally, due to difficult-to-access anatomy such as the cerebral vasculature and the neurovasculature, the systems should have a small collapsed profile.

The risk of dislodging foreign bodies is also prevalent in certain surgical procedures. It is therefore further desirable that such emboli capture and removal apparatuses are similarly useful with surgical procedures such as, without limitation, cardiac valve replacement, cardiac bypass grafting, cardiac reduction, or aortic replacement.

SUMMARY OF THE INVENTION

In general, the disclosure relates to methods and apparatuses for filtering blood. Filtration systems are provided that include a proximal filter and a distal filter. The filtration systems can be catheter-based for insertion into a patient's vascular system.

One aspect of the disclosure is a catheter-based endovascular system and method of use for filtering blood that captures and removes particles caused as a result of a surgical or endovascular procedures. The method and system include a first filter placed in a first vessel within the patient's vascular system and a second filter placed in a second vessel within the patient's vascular system. In this manner, the level of particulate protection is thereby increased.

One aspect of the disclosure is an endovascular filtration system and method of filtering blood that protects the cerebral vasculature from embolisms instigated or foreign bodies dislodged during a surgical procedure. In this aspect, the catheter-based filtration system is disposed at a location in the patient's arterial system between the site of the surgical procedure and the cerebral vasculature. The catheter-based filtration system is inserted and deployed at the site to capture embolisms and other foreign bodies and prevent their travel to the patient's cerebral vasculature so as to avoid or minimize thromboembolic disorders such as a stroke.

One aspect of the disclosure is an endovascular filtration system and method of filtering blood that provides embolic protection to the cerebral vasculature during a cardiac or cardiothoracic surgical procedure. According to this aspect, the filtration system is a catheter-based system provided with a first filter and a second filter. The first filter is positioned within the brachiocephalic artery, between the aorta and the right common carotid artery, with the second filter being positioned within the left common carotid artery.

One aspect of the disclosure is a catheter-based endovascular filtration system including a first filter and a second filter, wherein the system is inserted into the patient's right brachial or right radial artery. The system is then advanced through the patient's right subclavian artery and into the brachiocephalic artery. At a position within the brachiocephalic trunk between the aorta and the right common carotid artery, the catheter-based system is manipulated to deploy the first filter. The second filter is then advanced through the deployed first filter into the aorta and then into the left common carotid artery. Once in position within the left common carotid artery the catheter-based system is further actuated to deploy the second filter. After the surgical procedure is completed, the second filter and the first filter are, respectively, collapsed and withdrawn from the arteries and the catheter-based filtration system is removed from the patient's vasculature.

One aspect of the disclosure is a catheter-based filtration system comprising a handle, a first sheath, a first filter, a second sheath and a second filter. The handle can be a single or multiple section handle. The first sheath is translatable relative to the first filter to enact deployment of the first filter in a first vessel. The second sheath is articulatable from a first configuration to one or more other configurations. The extent of articulation applied to the second sheath is determined by the anatomy of a second vessel to which access is to be gained. The second filter is advanced through the articulated second sheath and into the vessel accessed by the second sheath and, thereafter, deployed in the second vessel. Actuation of the first sheath relative to the first filter and articulation of the second filter is provided via the handle.

In some aspect the first sheath is a proximal sheath, the first filter is a proximal filter, the second sheath is a distal sheath, and the second filter is a distal filter. The proximal sheath is provided with a proximal hub housed within and in sliding engagement with the handle. Movement of the proximal hub causes translation of the proximal sheath relative to the proximal filter. The distal sheath includes a distal shaft section and a distal articulatable sheath section. A wire is provided from the handle to the distal articulatable sheath section. Manipulation of the handle places tension on the wire causing the distal articulatable sheath section to articulate from a first configuration to one or more other configurations.

In some aspects the proximal filter and the distal filter are both self-expanding. Movement of the proximal sheath relative to the proximal filter causes the proximal filter to expand and deploy against the inside wall of a first vessel. The distal filter is then advanced through the distal shaft and distal articulatable sheath into expanding engagement against the inner wall of a second vessel.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIGS. 1A-1C illustrate an exemplary dual filter system.

FIGS. 1D and 1E illustrate exemplary proximal filters.

FIGS. 6A and 6B illustrate

FIGS. 7A and 7B illustrate a portion of an exemplary filter system.

FIGS. 8A-8C illustrate an exemplary pullwire.

FIGS. 10A and 10B illustrate a portion of exemplary distal sheath adapted to be multi-directional.

FIGS. 23A-23F illustrate exemplary distal filters.

FIGS. 24A-24C illustrate exemplary embodiments in which the system includes at least one distal filter positioning, or stabilizing, anchor.

FIGS. 27A and 27B illustrate an exemplary embodiment in which a guiding member, secured to a distal filter before introduction into the subject is loaded into an articulatable distal sheath.

FIGS. 29A-29E illustrate a portion of an exemplary filter system with a lower delivery and insertion profile.

FIGS. 30A and 30B illustrate a portion of an exemplary filter system.

FIGS. 31A-31C illustrate an exemplary over-the-wire routing system that includes a separate distal port for a dedicated guidewire.

DETAILED DESCRIPTION

The disclosure relates generally to intravascular blood filters used to capture foreign particles. In some embodiments the blood filter is a dual-filter system to trap foreign bodies to prevent them from traveling into the subject's right and left common carotid arteries. The filter systems described herein can, however, be used to trap particles in other blood vessels within a subject, and they can also be used outside of the vasculature. The systems described herein are generally adapted to be delivered percutaneously to a target location within a subject, but they can be delivered in any suitable way, and need not be limited to minimally-invasive procedures.

Figure 1:
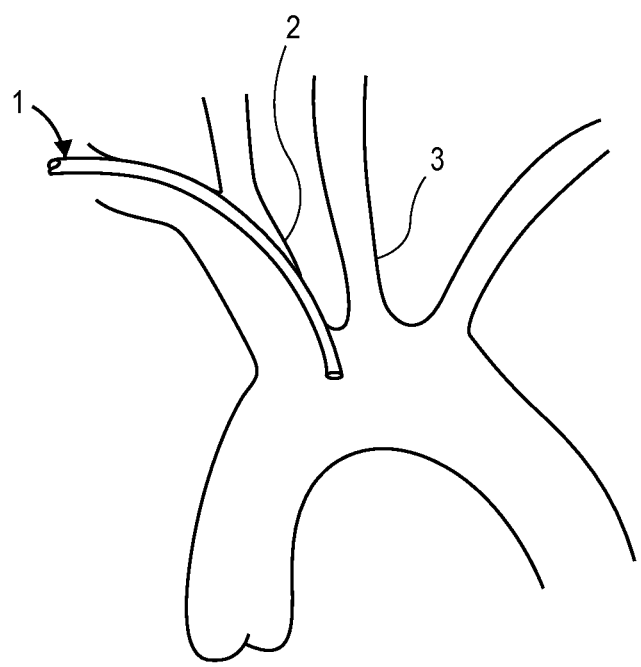
FIG. 1 illustrates an exemplary prior art catheter being advanced through a portion of a subject's vasculature.

In one application, the filter systems described herein are used to protect the cerebral vasculature against embolisms and other foreign bodies entering the bloodstream during a cardiac valve replacement or repair procedure. To protect both the right common carotid artery and the left common carotid artery during such procedures, the system described herein enters the aorta from the brachiocephalic artery. Once in the aortic space, there is a need to immediately navigate a 180 degree turn into the left common carotid artery. In gaining entry into the aorta from the brachial cephalic artery, use of prior art catheter devices 1 will tend to hug the outer edge of the vessel 2, as shown in FIG. 1. To then gain access to the left common carotid artery 3 with such prior art devices can be a difficult maneuver due to the close proximity of the two vessels which may parallel one another, often within 1 cm of separation, as shown in, for example, FIGS. 1-5. This sharp turn requires a very small radius and may tend to kink the catheter reducing or eliminating a through lumen to advance accessories such as guidewires, filters, stents, and other interventional tools. The catheter-based filter systems described herein can traverse this rather abrupt 180 degree turn to thereby deploy filters to protect both the right and left common carotid arteries.

FIGS. 1A and 1B illustrate a portion of an exemplary filter system. Filter system 10 includes proximal sheath 12, proximal shaft 14 coupled to expandable proximal filter 16, distal shaft 18 coupled to distal articulatable sheath 20, distal filter 22, and guiding member 24. FIG. 1A illustrates proximal filter 16 and distal filter 22 in expanded configurations. FIG. 1B illustrates the system in a delivery configuration, in which proximal filter 16 (not seen in FIG. 1B) is in a collapsed configuration constrained within proximal sheath 12, while distal filter 22 is in a collapsed configuration constrained within distal articulatable sheath 20.

FIG. 1C is a sectional view of partial system 10 from FIG. 1B. Proximal shaft 14 is co-axial with proximal sheath 12, and proximal region 26 of proximal filter 16 is secured to proximal shaft 14. In its collapsed configuration, proximal filter 16 is disposed within proximal sheath 12 and is disposed distally relative to proximal shaft 14. Proximal sheath 12 is axially (distally and proximally) movable relative to proximal shaft 14 and proximal filter 16. System 10 also includes distal sheath 20 secured to a distal region of distal shaft 18. Distal shaft 18 is co-axial with proximal shaft 14 and proximal sheath 12. Distal sheath 20 and distal shaft 18, secured to one another, are axially movable relative to proximal sheath 12, proximal shaft 14 and proximal filter 16. System 10 also includes distal filter 22 carried by guiding member 24. In FIG. 1C, distal filter 22 is in a collapsed configuration within distal sheath 22. Guiding member 24 is coaxial with distal sheath 20 and distal shaft 18 as well as proximal sheath 12 and proximal shaft 14. Guiding member 24 is axially movable relative to distal sheath 20 and distal shaft 18 as well as proximal sheath 12 and proximal shaft 14. Proximal sheath 12, distal sheath 20, and guiding member 24 are each adapted to be independently moved axially relative to one other. That is, proximal sheath 12, distal sheath 20, and guiding member 24 are adapted for independent axial translation relative to each of the other two components.

In the embodiments in FIGS. 1A-1E, proximal filter 16 includes support element or frame 15 and filter element 17, while distal filter 22 includes support element 21 and filter element 23. The support elements generally provide expansion support to the filter elements in their respective expanded configurations, while the filter elements are adapted to filter fluid, such as blood, and trap particles flowing therethrough. The expansion supports are adapted to engage the wall of the lumen in which they are expanded. The filter elements have pores therein that are sized to allow the blood to flow therethrough, but are small enough to prevent unwanted foreign particles from passing therethrough. The foreign particles are therefore trapped by and within the filter elements.

Figure 1D:
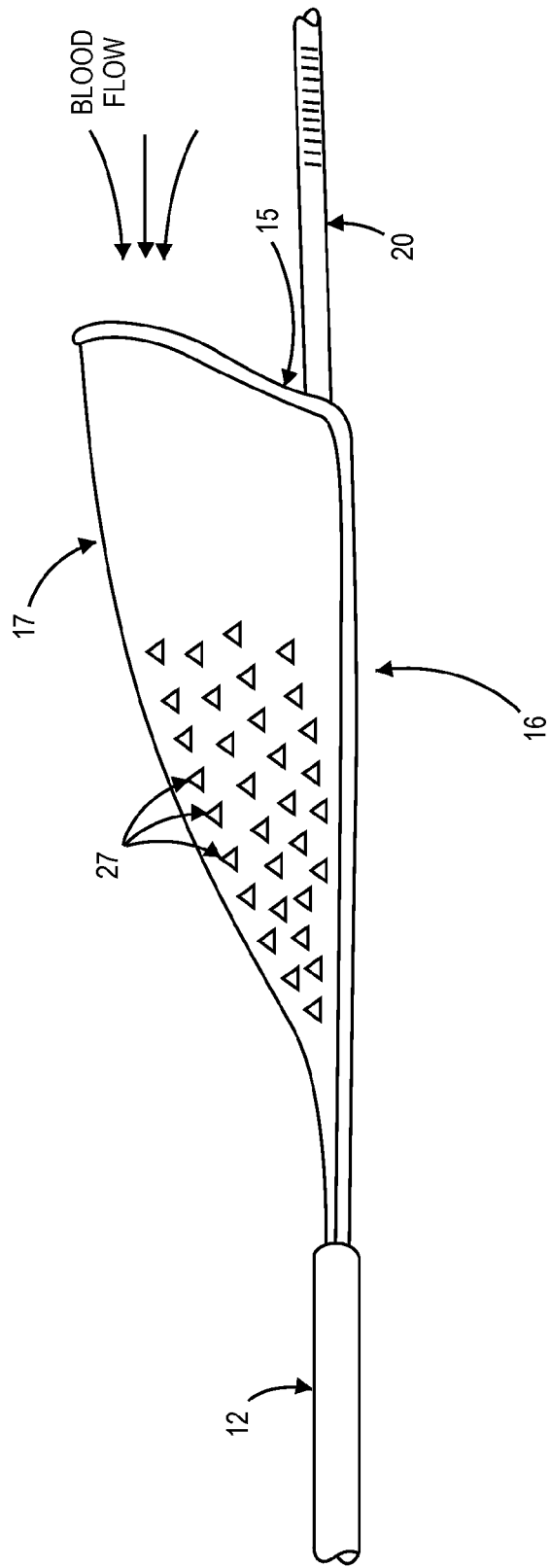

In one embodiment of the construction of the filter elements, filter element 17 is formed of a polyurethane film mounted to frame 15, as shown in FIGS. 1D and 1E. Film element 17 can measure about 0.0030 inches to about 0.0003 inches in thickness. Filter element 17 has through holes 27 to allow fluid to pass and will resist the embolic material within the fluid. These holes can be circular, square, triangular or other geometric shapes. In the embodiment as shown in FIG. 1D, an equilateral triangular shape would restrict a part larger than an inscribed circle but have an area for fluid flow nearly twice as large making the shape more efficient in filtration verses fluid volume. It is understood that similar shapes such as squares and slots would provide a similar geometric advantage.

Frame element 15 can be constructed of a shape memory material such as Nitinol, stainless steel or MP35N or a polymer that has suitable material properties. Frame element 15 could take the form of a round wire or could also be of a rectangular or elliptical shape to preserve a smaller delivery profile. In one such embodiment, frame element 15 is of Nitinol wire where the hoop is created from a straight piece of wire and shape set into a frame where two straight legs run longitudinally along the delivery system and create a circular distal portion onto which the filter film will be mounted. The circular portion may have a radiopaque marking such as a small coil of gold or platinum iridium for visualization under fluoroscopy.

Figure 25A:
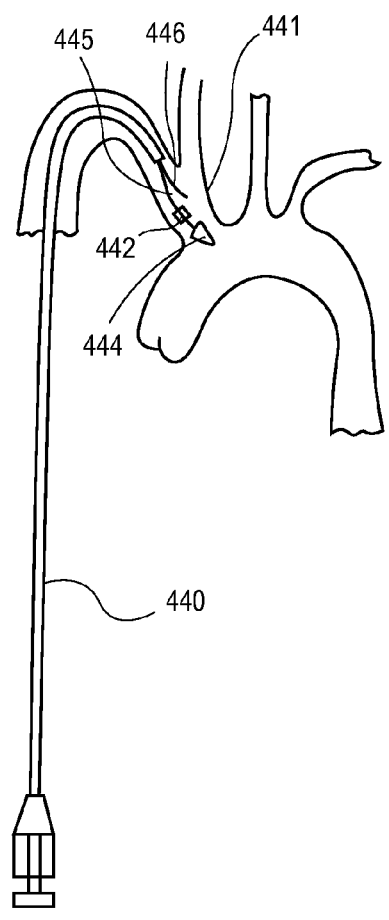
FIGS. 25A-25D illustrate an exemplary embodiment of coupling a distal filter to a docking wire inside of the subject.
Figure 25B:
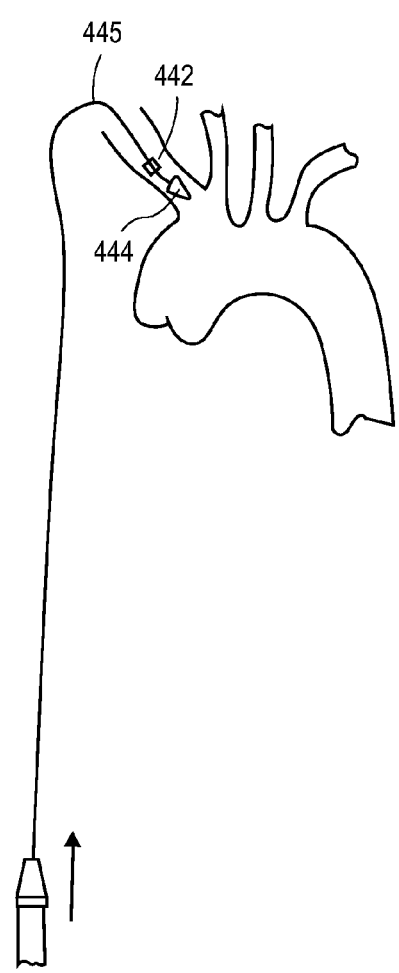
Figure 25C:
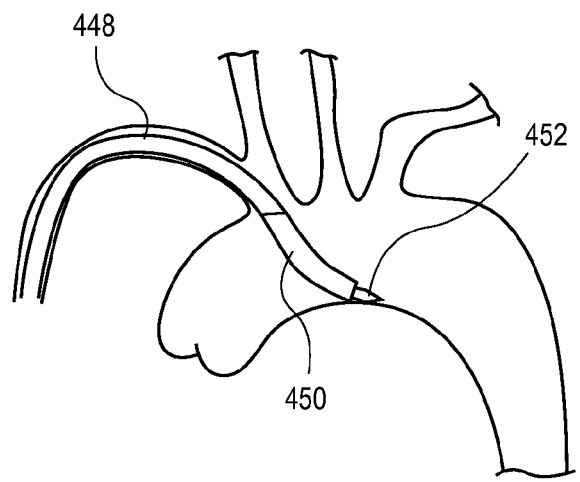
Figure 25D:
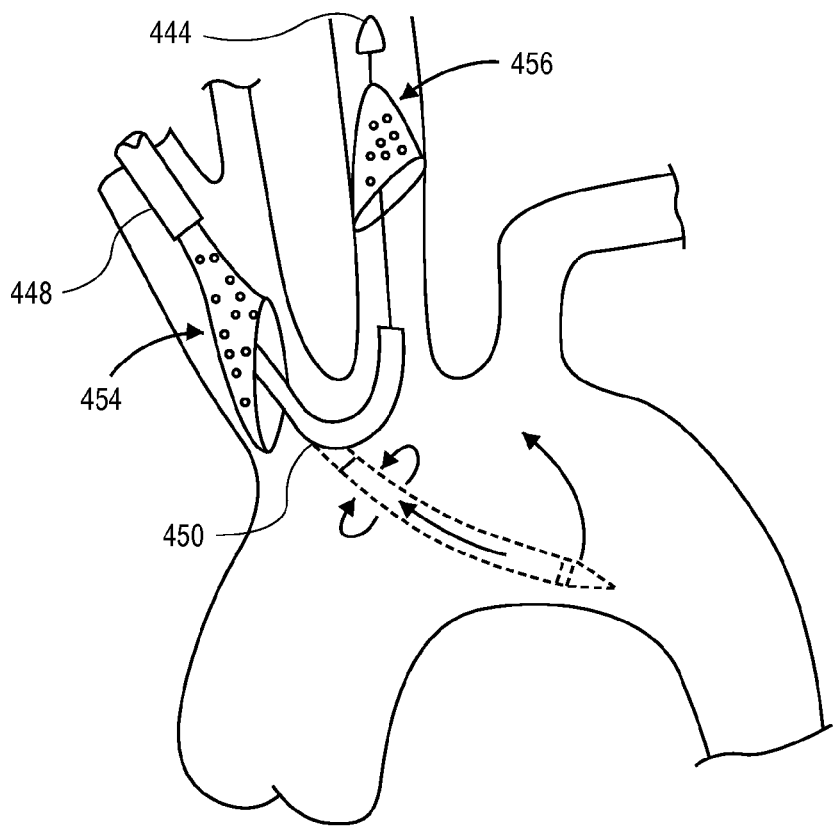

In some embodiments, such as those illustrated in FIGS. 1D, 1E and 25D, the shape of frame element 15 and filter element 17 are of an oblique truncated cone having a non-uniform or unequal length around and along the length of the conical filter 16. In such a configuration, much like a windsock, the filter 16 would have a larger opening diameter and a reduced ending diameter. In one embodiment, the larger opening diameter could measure about 15-20 mm in diameter and have a length of about 30-50 mm. Varying size filters would allow treatment of variable patient vessel sizes.

It some embodiments the material of the filter element is a smooth textured surface that is folded or contracted into a small delivery catheter by means of tension or compression into a lumen. A reinforcement fabric 29, as shown in FIG. 1E, may be added to or embedded in the filter to accommodate stresses placed on the filter material by means of the tension or compression applied. This will also reduce the stretching that may occur during delivery and retraction of filter element 17. This reinforcement material 29 could be a polymer or metallic weave to add additional localized strength. This material could be imbedded into the polyurethane film to reduce its thickness. In one particular embodiment, this imbedded material could be polyester weave with a pore size of about 100 microns and a thickness of about 0.002 inches and mounted to a portion of the filter near the longitudinal frame elements where the tensile forces act upon the frame and filter material to expose and retract the filter from its delivery system. While such an embodiment of the filter elements has been described for convenience with reference to proximal filter element 17, it is understood that distal filter element 23 could similarly take such form or forms.

As shown in FIG. 1A, proximal filter 16 has a generally distally-facing opening 13, and distal filter 22 has a generally proximally-facing opening 19. The filters can be thought of as facing opposite directions. As described in more detail below, the distal sheath is adapted to be steered, or bent, relative to the proximal sheath and the proximal filter. As the distal sheath is steered, the relative directions in which the openings face will be adjusted. Regardless of the degree to which the distal sheath is steered, the filters are still considered to having openings facing opposite directions. For example, the distal sheath could be steered to have a 180 degree bend, in which case the filters would have openings facing in substantially the same direction. The directions of the filter openings are therefore described if the system were to assume a substantially straightened configuration, an example of which is shown in FIG. 1A. Proximal filter element 17 tapers down in the proximal direction from support element 15, while distal filter element 23 tapers down in the distal direction from support element 21. A fluid, such as blood, flows through the opening and passes through the pores in the filter elements, while the filter elements are adapted to trap foreign particles therein and prevent their passage to a location downstream to the filters.

In some embodiments the filter pores are between about 1 micron and 1000 microns (1 mm). The pore size can be larger, however, depending on the location of the filter within the subject and the type of particulate being trapped in the filter.

The filters are secured to separate system components. In the embodiment in FIGS. 1A-1C, for example, proximal filter 16 is secured to proximal shaft 14, while distal filter 22 is secured to guiding member 24. In FIGS. 1A-1C, the filters are secured to independently-actuatable components. This allows the filters to be independently controlled. Additionally, the filters are collapsed within two different tubular members in their collapsed configurations. In the embodiment in FIGS. 1A-1C, for example, proximal filter 16 is collapsed within proximal sheath 12, while distal filter 22 is collapsed within distal sheath 20. In the system's delivery configuration, the filters are axially-spaced from one another. For example, in FIG. 1C, distal filter 22 is distally-spaced relative to proximal filter 16.

In some embodiments the distal sheath and the proximal sheath have substantially the same outer diameter (see, e.g., FIGS. 1B and 1C). When the filters are collapsed within the sheaths, the sheath portion of the system therefore has a substantially constant outer diameter, which can ease the delivery of the system through the patient's body and increase the safety of the delivery. In FIG. 1C, distal and proximal sheaths 20 and 12 have substantially the same outer diameter, both of which have larger outer diameters than the proximal shaft 14. Proximal shaft 14 has a larger outer diameter than distal shaft 18, wherein distal shaft 18 is disposed within proximal shaft 14. Guiding member 24 has a smaller diameter than distal shaft 18. In some embodiments the proximal and distal sheaths have an outer diameter of 6 French (F). In some embodiments the sheaths have different outer diameters. For example, the proximal sheath can have a size of 6 F, while the distal sheath has a size of 5 F. In an alternative embodiment the proximal sheath is 5 F and the distal sheath is 4 F. A distal sheath with a smaller outer diameter than the proximal sheath reduces the delivery profile of the system and can ease delivery.

In some methods of use, the filter system is advanced into the subject through an incision made in the subject's right radial artery. In a variety of medical procedures a medical instrument is advanced through a subject's femoral artery, which is larger than the right radial artery. A delivery catheter used in femoral artery access procedures has a larger outer diameter than would be allowed in a filter system advanced through a radial artery. Additionally, in some uses the filter system is advanced from the right radial artery into the aorta via the brachiocephalic trunk. The radial artery has the smallest diameter of the vessels through which the system is advanced. The radial artery therefore limits the size of the system that can be advanced into the subject when the radial artery is the access point. The outer diameters of the systems described herein, when advanced into the subject via a radial artery, are therefore smaller than the outer diameters of the guiding catheters (or sheaths) typically used when access is gained via a femoral artery.

FIG. 6A illustrates a portion of a filter delivery system in a delivery configuration. The system's delivery configuration generally refers to the configuration when both filters are in collapsed configurations within the system. FIG. 6B illustrates that that the distal articulating sheath is independently movable with 3 degrees of freedom relative to the proximal sheath and proximal filter. In FIG. 6A, proximal sheath 60 and distal sheath 62 are coupled together at coupling 61. Coupling 61 can be a variety of mechanisms to couple proximal sheath 60 to distal sheath 62. For example, coupling 61 can be an interference fit, a friction fit, a spline fitting, or any other type of suitable coupling between the two sheaths. When coupled together, as shown in FIG. 6A, the components shown in FIG. 6B move as a unit. For example, proximal sheath 60, proximal shaft 64, proximal filter 66, distal shaft 68, and the distal filter (not shown but within distal sheath 62) will rotate and translate axially (in the proximal or distal direction) as a unit. When proximal sheath 60 is retracted to allow proximal filter 66 to expand, as shown in FIG. 6B, distal sheath 62 can be independently rotated ("R"), steered ("S"), or translated axially T (either in the proximal "P" direction or distal "D" direction). The distal sheath therefore has 3 independent degrees of freedom: axial translation, rotation, and steering. The adaptation to have 3 independent degrees of freedom is advantageous when positioning the distal sheath in a target location, details of which are described below.

Figure 2B:
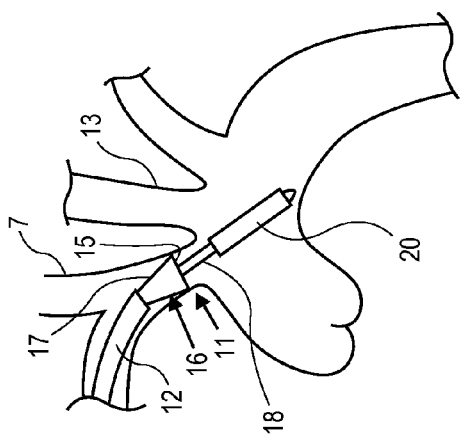
FIGS. 2A-2D illustrate an exemplary method of delivering and deploying a dual filter system
Figure 2D:
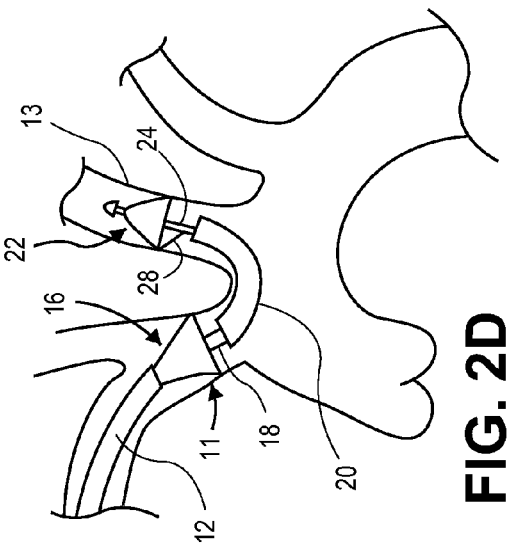
Figure 2A:
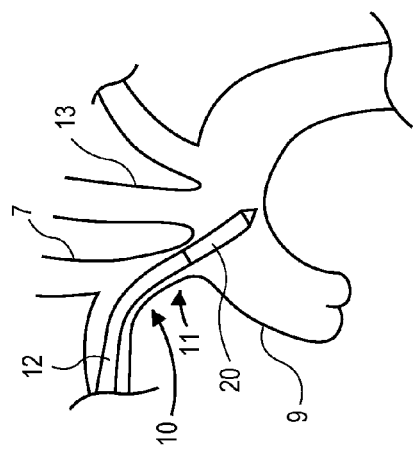
Figure 2C:
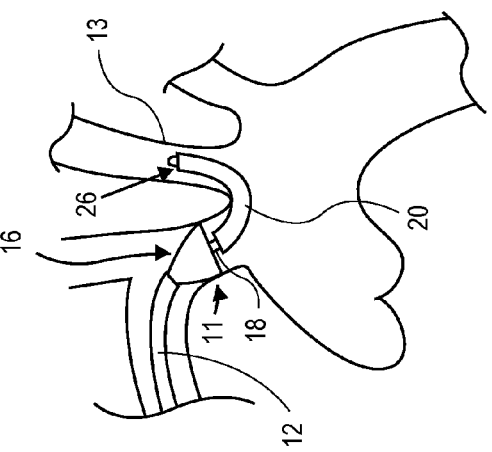

FIGS. 2A-2D illustrate a merely exemplary embodiment of a method of using any of the filter systems described herein. System 10 from FIGS. 1A-1C is shown in the embodiment in FIGS. 2A-2D. System 10 is advanced into the subject's right radial artery through an incision in the right arm. The system is advanced through the right subclavian artery and into the brachiocephalic trunk 11, and a portion of the system is positioned within aorta 9 as can be seen in FIG. 2A (although that which is shown in FIG. 2A is not intended to be limiting). Proximal sheath 12 is retracted proximally to allow proximal filter support element 15 to expand to an expanded configuration against the wall of the brachiocephalic trunk 11, as is shown in FIG. 2B. Proximal filter element 17 is secured either directly or indirectly to support element 15, and is therefore reconfigured to the configuration shown in FIG. 2B. The position of distal sheath 20 can be substantially maintained while proximal sheath 12 is retracted proximally. Once expanded, the proximal filter filters blood traveling through the brachiocephalic artery 11, and therefore filters blood traveling into the right common carotid artery 7. The expanded proximal filter is therefore in position to prevent foreign particles from traveling into the right common carotid artery 7 and into the cerebral vasculature. Distal sheath 20 is then steered, or bent, and distal end 26 of distal sheath 20 is advanced into the left common carotid artery 13, as shown in FIG. 2C. Guiding member 24 is thereafter advanced distally relative to distal sheath 20, allowing the distal support element to expand from a collapsed configuration against the wall of the left common carotid artery 13 as shown in FIG. 2D. The distal filter element is also reconfigured into the configuration shown in FIG. 2D. Once expanded, the distal filter filters blood traveling through the left common carotid artery 13. The distal filter is therefore in position to trap foreign particles and prevent them from traveling into the cerebral vasculature.

Once the filters are in place and expanded, an optional medical procedure can then take place, such as a replacement heart valve procedure. Any plaque dislodged during the heart valve replacement procedure that enters into the brachiocephalic trunk or the left common carotid artery will be trapped in the filters.

The filter system can thereafter be removed from the subject (or at any point in the procedure). In an exemplary embodiment, distal filter 22 is first retrieved back within distal sheath 20 to the collapsed configuration. To do this, guiding member 24 is retracted proximally relative to distal sheath 20. This relative axial movement causes distal sheath 20 to engage strut 28 and begin to move strut 28 towards guiding member 24. Support element 21, which is coupled to strut 28, begins to collapse upon the collapse of strut 28. Filter element 23 therefore begins to collapse as well. Continued relative axial movement between guiding member 24 and distal sheath 20 continues to collapse strut 28, support element 21, and filter element 23 until distal filter 22 is retrieved and re-collapsed back within distal sheath 20 (as shown in FIG. 2C). Any foreign particles trapped within distal filter element 23 are contained therein as the distal filter is re-sheathed. Distal sheath 20 is then steered into the configuration shown in FIG. 2B, and proximal sheath is then advanced distally relative to proximal filter 16. This causes proximal filter 16 to collapse around distal shaft 18, trapping any particles within the collapsed proximal filter. Proximal sheath 12 continues to be moved distally towards distal sheath 20 until in the position shown in FIG. 2A. The entire system 10 can then be removed from the subject.

An exemplary advantage of the systems described herein is that the delivery and retrieval system are integrated into the same catheter that stays in place during the procedure. Unloading and loading of different catheters, sheaths, or other components is therefore unnecessary. Having a system that performs both delivery and retrieval functions also reduces procedural complexity, time, and fluoroscopy exposure time.

FIGS. 7A-7B illustrate a perspective view and sectional view, respectively, of a portion of an exemplary filter system. The system includes distal shaft 30 and distal articulatable sheath 34, coupled via coupler 32. FIG. 7B shows the sectional view of plane A. Distal sheath 34 includes steering element 38 extending down the length of the sheath and within the sheath, which is shown as a pullwire. The pullwire can be, for example without limitation, stainless steel, MP35N®, or any type of cable. Distal sheath 34 also includes spine element 36, which is shown extending down the length of the sheath on substantially the opposite side of the sheath from steering element 38. Spine element 36 can be, for example without limitation, a ribbon or round wire. Spine element 36 can be made from, for example, stainless steel or nitinol. Spine element 36 provides axial stiffness upon the application of an actuating force applied to steering element 38, allowing sheath 34 to be steered toward configuration 40, as shown in phantom in FIG. 7A. FIG. 7C shows an alternative embodiment in which distal sheath 33 has a non-circular cross section. Also shown are spine element 35 and steering element 37.

FIGS. 8A-8C illustrate views of exemplary pullwire 42 that can be incorporated into any distal sheaths described herein. Plane B in FIG. 8B shows a substantially circular cross-sectional shape of pullwire 42 in a proximal portion 44 of the pullwire, while plane C in FIG. 8C shows a flattened cross-sectional shape of distal portion 46. Distal portion 46 has a greater width than height. The flattened cross-sectional shape of distal portion 46 provides for an improved profile, flexibility, and resistance to plastic deformation, which provides for improved straightening.

Figure 9A:
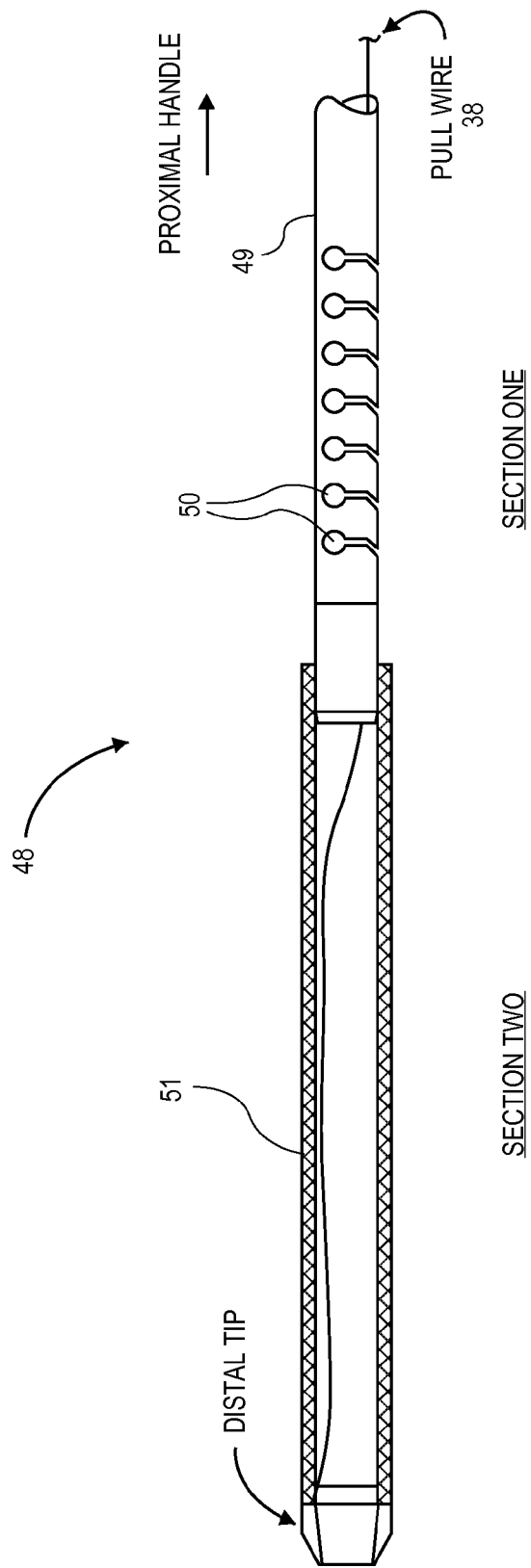
FIGS. 9, 9A, and 9B show an exemplary embodiment of a distal sheath with slots formed therein
Figure 9B:
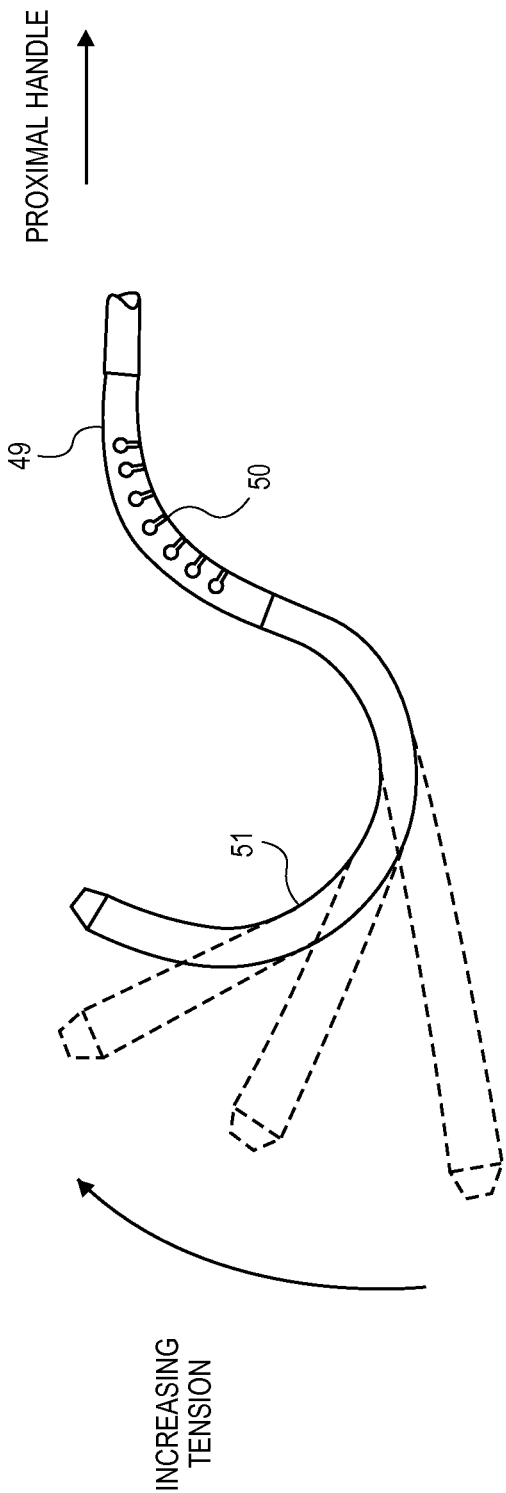
Figure 9C:
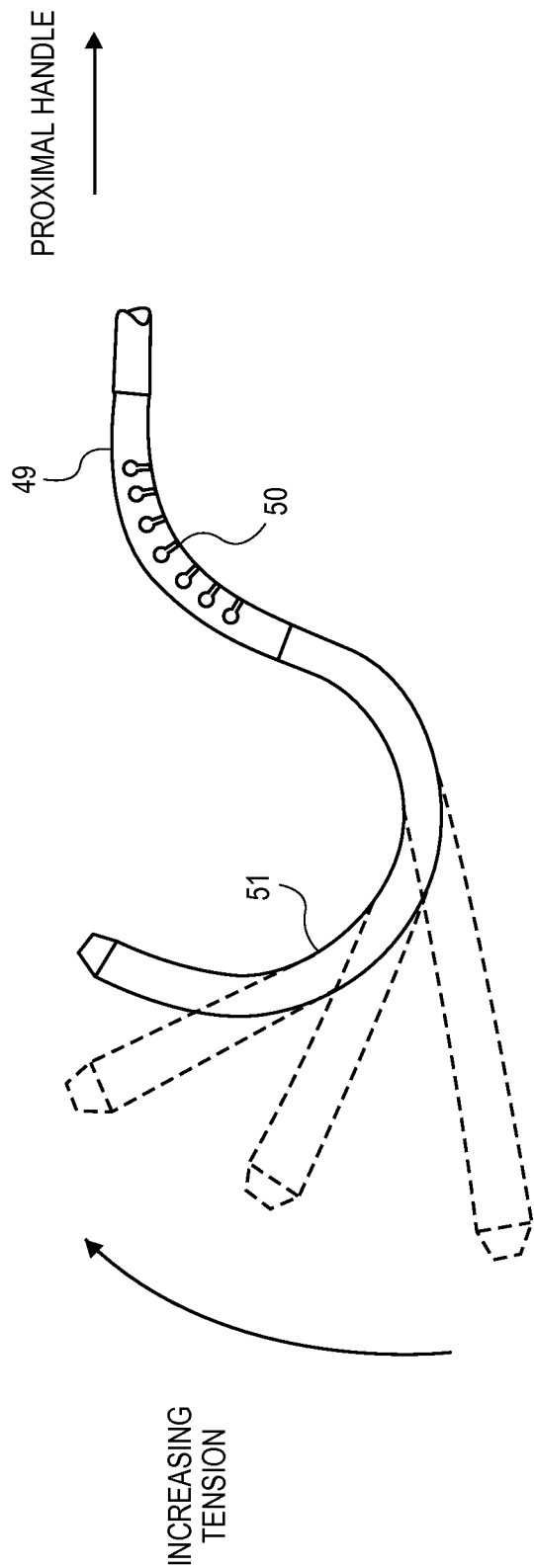

FIGS. 9, 9A, and 9B show an alternative embodiment of distal sheath 48 that includes slots 50 formed therein. The slots can be formed by, for example, grinding, laser cutting or other suitable material removal from distal sheath 48. The characteristics of the slots can be varied to control the properties of the distal sheath. For example, the pitch, width, depth, etc., of the slots can be modified to control the flexibility, compressibility, torsional responsiveness, etc., of distal sheath 48. More specifically, the distal sheath 48 can be formed from a length of stainless steel hypotubing. Transverse slots 50 are preferably formed on one side of the hypotubing.

FIG. 9A shows a further embodiment of the distal sheath in greater detail. In this embodiment distal sheath 48 includes a first proximal articulatable hypotube section 49. Articulatable hypotube section 49 is fixed to distal shaft 30 (not shown in FIG. 9A). A second distal articulatable section 51 is secured to first proximal section 49. Pull wire 38 extends from the handle to both distal shaft sections 49 and 51. This embodiment allows for initial curvature of distal sheath proximal section 49 away from the outer vessel wall. Distal sheath distal section 51 is then articulated to a second curvature in the opposite direction. This second curvature of distal shaft section 51 is adjustable based upon tension or compression loading of the sheath section by pull wire 38.

As shown in FIG. 9A, pull wire 38 crosses to an opposite side of the inner lumen defined by sections 49 and 51 as it transitions from the first proximal distal sheath section 49 to distal sheath distal section 51. As best shown in FIG. 9B, distal sheath proximal section 49 would articulate first to initialize a first curve. And, as the tension on pull wire 38 is increased, distal sheath distal section 51 begins to curve in a direction opposite to the direction of the first curve, due to pull wire 38 crossing the inner diameter of the lumen through distal sheath sections 49 and 51. As can be seen in FIG. 9B, as it nears and comes to the maximum extent of its articulation, distal sheath distal section 51 can take the form of a shepherd's staff or crook.

Distal sheath proximal section 49 could take the form of a tubular slotted element or a pre-shaped curve that utilizes a memory material such as Nitinol. Distal sheath proximal section 49, in one particular embodiment, measures about 0.065 inches in diameter with an about 0.053 inch hole through the center and measures about 0.70 inches in length. It is understood that these sizes and proportions will vary depending on the specific application and those listed herein are not intended to be limiting. Transverse slots 50 can measure about 0.008 inches in width but may vary from about 0.002 inches to about 0.020 inches depending on the specific application and the degree of curvature desired. In one embodiment distal shaft proximal section 49 is a laser cut tube intended to bend to approximately 45 degrees of curvature when pull wire 38 is fully tensioned. This curvature may indeed be varied from about 15 degrees to about 60 degrees depending upon the width of slots 50. It may also bend out-of-plane to access more complex anatomy. This out-of-plane bend could be achieved by revolving the laser cut slots rotationally about the axis of the tube or by bending the tube after the laser cutting of the slots. The shape could also be multi-plane or bidirectional where the tube would bend in multiple directions within the same laser cut tube.

Distal sheath distal section 51 is preferably a selectable curve based upon the anatomy and vessel location relative to one another. This section 51 could also be a portion of the laser cut element or a separate construction where a flat ribbon braid could be utilized. It may also include a stiffening element or bias ribbon to resist permanent deformation. In one embodiment it would have a multitude of flat ribbons staggered in length to create a constant radius of curvature under increased loading.

FIGS. 10A and 10B illustrate a portion of exemplary distal sheath 52 that is adapted to be multi-directional, and is specifically shown to be bi-directional. Distal sheath 52 is adapted to be steered towards the configurations 53 and 54 shown in phantom in FIG. 10A. FIG. 10B is a sectional view in plane D, showing spinal element 55 and first and second steering elements 56 disposed on either side of spinal element 55. Steering elements 56 can be similar to steering element 38 shown in FIG. 7B. The steering elements can be disposed around the periphery of distal sheath at almost any location.

Incorporating steerable functionality into tubular devices is known in the area of medical devices. Any such features can be incorporated into the systems herein, and specifically into the articulatable distal sheaths.

In some embodiments the distal sheath includes radiopaque markers to visualize the distal sheath under fluoroscopy. In some embodiments the distal sheath has radiopaque markers at proximal and distal ends of the sheath to be able to visualize the ends of the sheath.

Figure 11A:
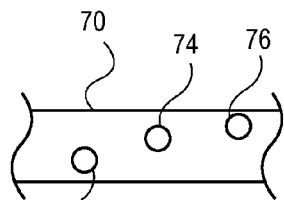
FIGS. 11A-11C illustrate merely exemplary anatomical variations that can exist.
Figure 11B:
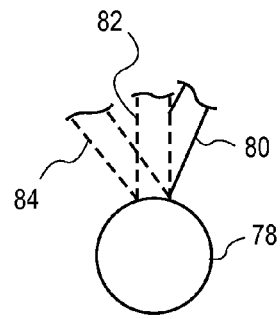
Figure 11C:
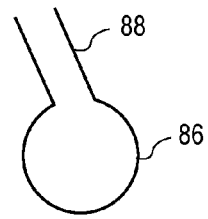
Figure 11D:
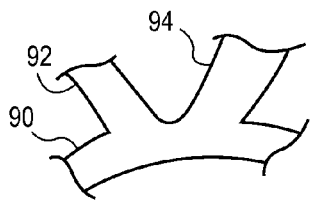
Figure 11E:
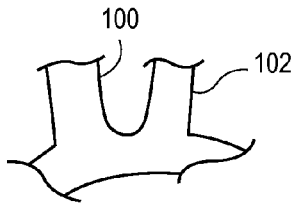

An exemplary advantage of the filter systems described herein is the ability to safely and effectively position the distal sheath. In some uses, the proximal filter is deployed in a first bodily lumen, and the distal filter is deployed in a second bodily lumen different than the first. For example, as shown in FIG. 2D, the proximal filter is deployed in the brachiocephalic trunk and the distal filter is deployed in a left common carotid artery. While both vessels extend from the aortic arch, the position of the vessel openings along the aortic arch varies from patient-to-patient. That is, the distance between the vessel openings can vary from patient to patient. Additionally, the angle at which the vessels are disposed relative to the aorta can vary from patient to patient. Additionally, the vessels do not necessarily lie within a common plane, although in many anatomical illustrations the vessels are typically shown this way. For example, FIGS. 11A-11C illustrate merely exemplary anatomical variations that can exist. FIG. 11A is a top view (i.e., in the superior-to-inferior direction) of aorta 70, showing relative positions of brachiocephalic trunk opening 72, left common carotid artery opening 74, and left subclavian opening 76. FIG. 11B is a side sectional view of aortic 78 illustrating the relative angles at which brachiocephalic trunk 80, left common carotid artery 82, and left subclavian artery 84 can extend from aorta 78. FIG. 11C is a side sectional view of aorta 86, showing vessel 88 extending from aorta 86 at an angle. Any or all of the vessels extending from aorta 86 could be oriented in this manner relative to the aorta. FIGS. 11D and 11E illustrate that the angle of the turn required upon exiting the brachiocephalic trunk 92/100 and entering the left common carotid artery 94/102 can vary from patient to patient. Due to the patient-to-patient variability between the position of the vessels and their relative orientations, a greater amount of control of the distal sheath increases the likelihood that the distal filter will be positioned safely and effectively. For example, a sheath that only has the ability to independently perform one or two of rotation, steering, and axial translation may not be adequately adapted to properly and safely position the distal filter in the left common carotid artery. All three degrees of independent motion as provided to the distal sheaths described herein provide important clinical advantages. Typically, but without intending to be limiting, a subject's brachiocephalic trunk and left carotid artery are spaced relatively close together and are either substantially parallel or tightly acute (see, e.g., Figure BE).

Figure 12A:
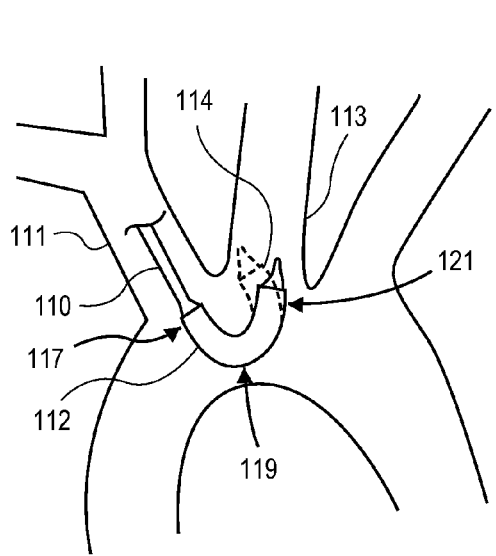
FIGS. 12A and 12B illustrate an exemplary curvature of a distal sheath to help position the distal filter properly in the left common carotid artery.
Figure 12B:
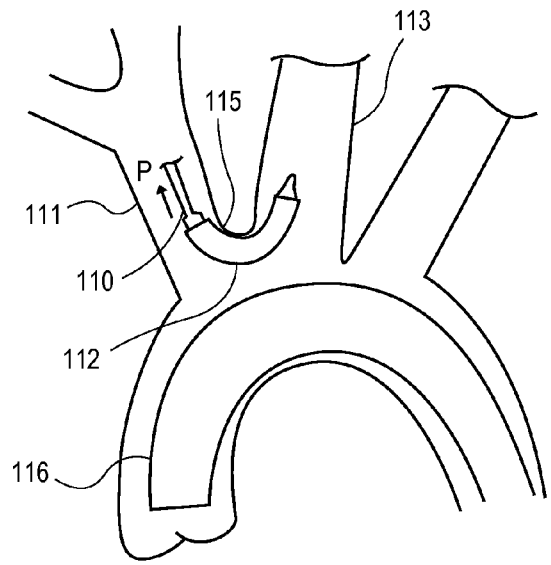

FIGS. 12A and 12B illustrates an exemplary curvature of a distal sheath to help position the distal filter properly in the left common carotid artery. In FIGS. 12A and 12B, only a portion of the system is shown for clarity, but it can be assumed that a proximal filter is included, and in this example has been expanded in brachiocephalic trunk 111. Distal shaft 110 is coupled to steerable distal sheath 112. Distal sheath 112 is steered into the configuration shown in FIG. 12B. The bend created in distal sheath 112, and therefore the relative orientations of distal sheath 112 and left common carotid artery 113, allow for the distal filter to be advanced from distal sheath 112 into a proper position in left common carotid 113. In contrast, the configuration of distal sheath 114 shown in phantom in FIG. 12A illustrates how a certain bend created in the distal sheath can orient the distal sheath in such a way that the distal filter will be advanced directly into the wall of the left common carotid (depending on the subject's anatomy), which can injure the wall and prevent the distal filter from being properly deployed. Depending on the angulation, approach angle, spacing of the openings, etc., a general U-shaped curve (shown in phantom in FIG. 12A) may not be optimal for steering and accessing the left common carotid artery from the brachiocephalic trunk.

In some embodiments the distal sheath is adapted to have a preset curved configuration. The preset configuration can have, for example, a preset radius of curvature (or preset radii of curvature at different points along the distal sheath). When the distal sheath is articulated to be steered to the preset configuration, continued articulation of the steering element can change the configuration of the distal sheath until is assumes the preset configuration. For example, the distal sheath can comprise a slotted tube with a spine extending along the length of the distal sheath. Upon actuation of the steering component, the distal sheath will bend until the portions of the distal sheath that define the slots engage, thus limiting the degree of the bend of the distal sheath. The curve can be preset into a configuration that increases the likelihood that the distal filter will, when advanced from the distal sheath, be properly positioned within the left common carotid artery.

Figure 13A:
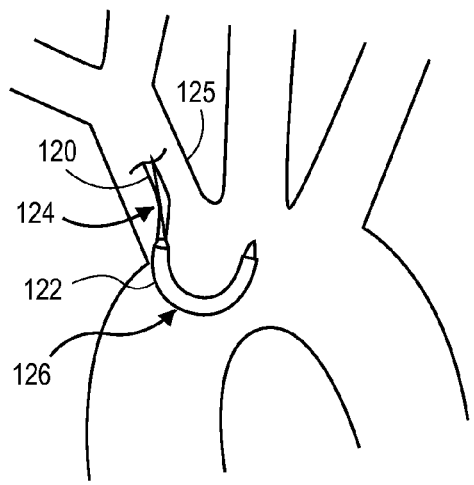
FIGS. 13A and 13B illustrate alternative distal sheath and distal shaft portions of an exemplary filter system.
Figure 13B:
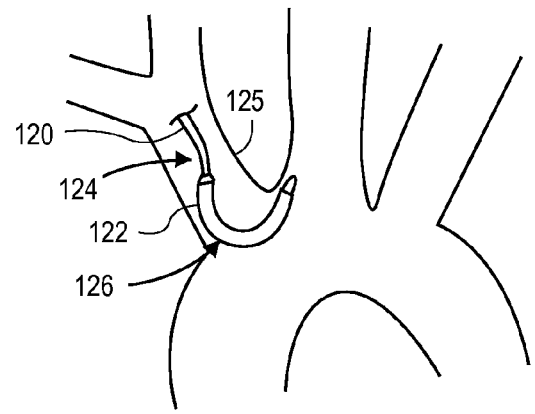

FIGS. 13A and 13B illustrate alternative distal sheath and distal shaft portions of an exemplary filter system. FIGS. 13A and 13B only show distal shaft 120 and distal sheath 122 for clarity, but the system also includes a proximal filter (not shown but has been deployed in brachiocephalic trunk). The distal shaft/distal sheath combination has a general S-bend configuration, with distal shaft 120 including a first bend 124 in a first direction, and distal sheath 122 configured to assume bend 126 in a second direction, wherein the first and second bends form the general S-bend configuration. FIG. 13B shows distal sheath 122 pulled back in the proximal direction relative to the proximal filter to seat the curved distal sheath against the bend. This both helps secure the distal sheath in place as well as reduces the cross sectional volume of the filter system that is disposed with the aorta. The distal shaft and distal sheath combination shown in FIGS. 13A and 13B can be incorporated into any of the filter systems described herein.

Exemplary embodiments of the delivery and deployment of a multi-filter embolic protection apparatus will now be described with reference to FIGS. 2A-2D, 13A, 13B, 14, 1, 3, 4 and 5. More particularly, the delivery and deployment will be described with reference to placement of the filter system in the brachiocephalic and left common carotid arteries. The preferred access for the delivery of the multi-filter system 10 is from the right radial or right brachial artery. The system is then advanced through the right subclavian artery to a position within the brachiocephalic artery 11. At this point, proximal filter 16 may be deployed within into expanding engagement with the inner lining of brachiocephalic artery 11. Alternatively, access to the left common carotid could be gained prior to deployment of proximal filter 16. Deployment of proximal filter 16 protects both the brachiocephalic artery 11 and the right common carotid artery 7 against emboli and other foreign bodies in the bloodstream.

Figure 3:
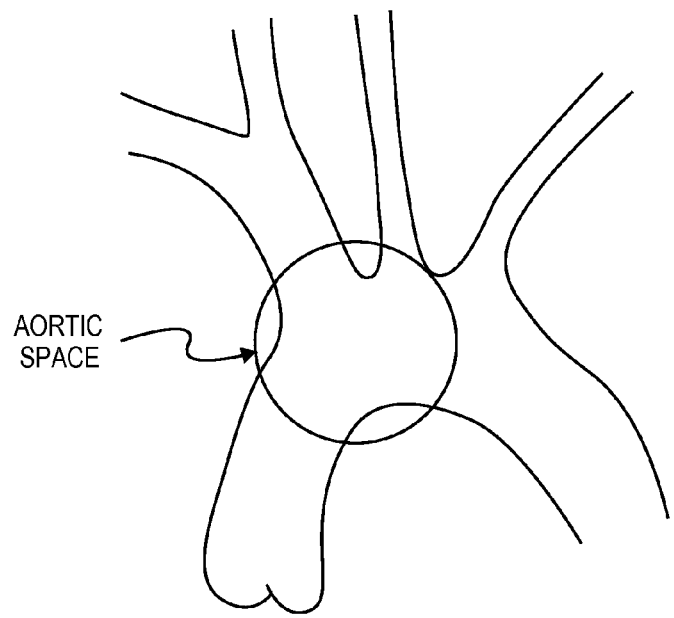
FIGS. 3-5 illustrate a portion of an exemplary delivery procedure for positioning a blood filter.
Figure 4:
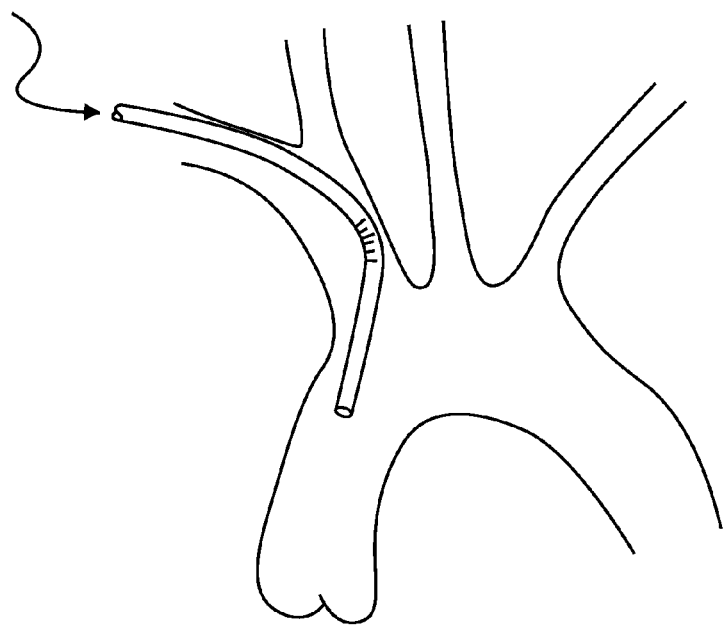
Figure 5:
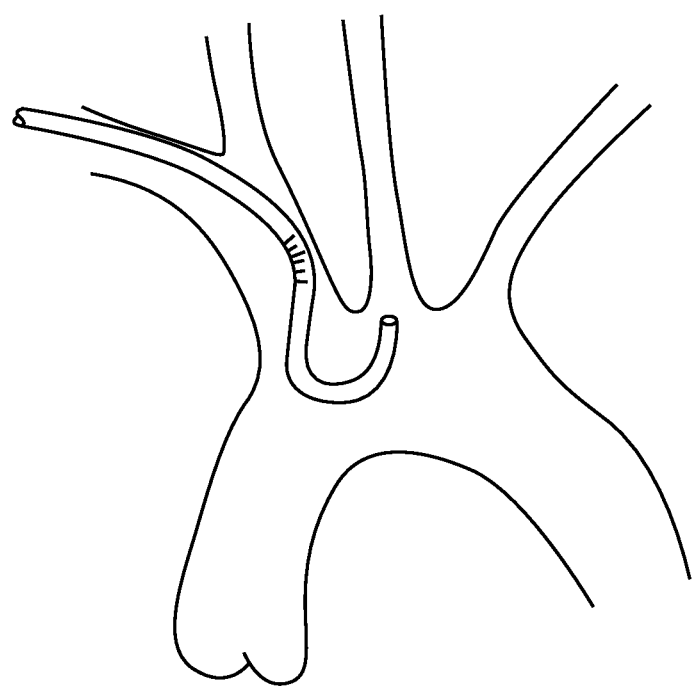

Entry into the aortic space, as illustrated in FIG. 3, is then accomplished by further advancement of the system from the brachiocephalic trunk. During this step, the filter system will tend to hug the outer portion of the brachiocephalic trunk as shown in FIG. 4. Initial tensioning of pull wire 38 causes distal sheath 48 to move the catheter-based filter system off the wall of the brachiocephalic artery just before the ostium or entrance into the aorta, as shown in FIG. 4. As the catheter path will hug the outer wall of the brachial cephalic artery, a curve directed away from this outer wall will allow additional space for the distal portion of the distal sheath to curve into the left common carotid artery, as shown in FIG. 5.

The width of slots 50 will determine the amount of bending allowed by the tube when tension is applied via pull wire 38. For example, a narrow width slot would allow for limited bending where a wider slot would allow for additional bending due to the gap or space removed from the tube. As the bending is limited by the slot width, a fixed shape or curve may be obtained when all slots are compressed and touching one another. Additional features such as chevrons may be cut into the tube to increase the strength of the tube when compressed. Theses chevrons would limit the ability of the tube to flex out of the preferred plane due to torsional loading. Other means of forming slots could be obtained with conventional techniques such as chemical etching, welding of individual elements, mechanical forming, metal injection molding or other conventional methods.

Once in the aortic space, the distal sheath is further tensioned to adjust the curvature of the distal shaft distal section 51, as shown in FIG. 9B. The amount of deflection is determined by the operator of the system based on the particular patient anatomy.

Other techniques to bias a catheter could be external force applications to the catheter and the vessel wall such as a protruding ribbon or wire from the catheter wall to force the catheter shaft to a preferred position within the vessel. Flaring a radial element from the catheter central axis could also position the catheter shaft to one side of the vessel wall. Yet another means would be to have a pull wire external to the catheter shaft exiting at one portion and reattaching at a more distal portion where a tension in the wire would bend or curve the catheter at a variable rate in relation to the tension applied.

This multi-direction and variable curvature of the distal sheath allows the operator to easily direct the filter system, or more particularly, the distal sheath section thereof, into a select vessel such as the left common carotid artery or the left innominate artery. Furthermore, the filter system allows the operator to access the left common carotid artery without the need to separately place a guidewire in the left common carotid artery. The clinical variations of these vessels are an important reason for the operator to have a system that can access differing locations and angulations between the vessels. The filter systems described herein will provide the physician complete control when attempting to access these vessels.

Once the distal sheath is oriented in the left common carotid, the handle can be manipulated by pulling it and the filter system into the bifurcation leaving the aortic vessel clear of obstruction for additional catheterizations, an example of which is shown in FIG. 12B. At this time, distal filter 22 can be advanced through proximal shaft 14 and distal shaft 18 into expanding engagement with left common carotid artery 13.

Figure 14:
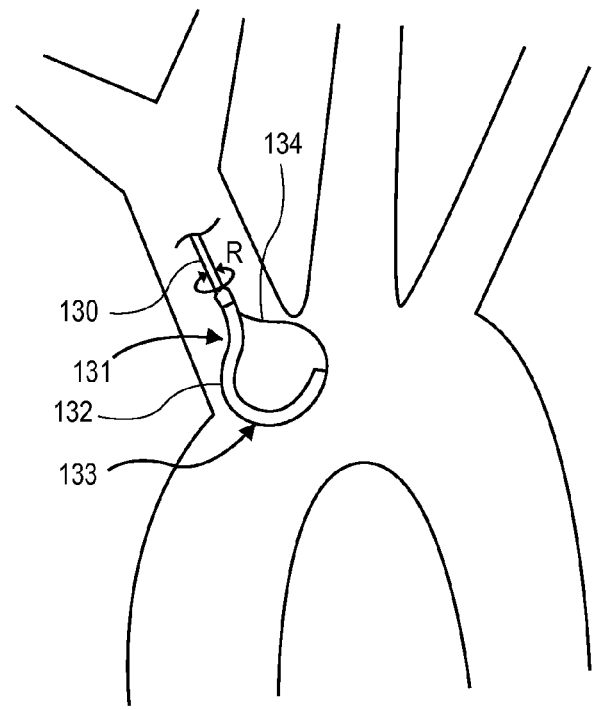
FIG. 14 illustrates a portion of an exemplary system including a distal shaft and a distal sheath.

FIG. 14 illustrates a portion of an exemplary system including distal shaft 130 and distal sheath 132. Distal sheath is adapted to be able to be steered into what can be generally considered an S-bend configuration, a shepherd's staff configuration, or a crook configuration, comprised of first bend 131 and second bend 133 in opposite directions. Also shown is rotational orb 134, defined by the outer surface of the distal sheath as distal shaft 130 is rotated at least 360 degrees in the direction of the arrows shown in FIG. 14. If a typical aorta is generally in the range from about 24 mm to about 30 mm in diameter, the radius of curvature and the first bend in the S-bend can be specified to create a rotational orb that can reside within the aorta (as shown in FIG. 14), resulting in minimal interference with the vessel wall and at the same time potentially optimize access into the left common carotid artery. In other distal sheath and/or distal shaft designs, such as the one shown in FIG. 12A, the rotational orb created by the rotation of distal shaft 110 is significantly larger, increasing the risk of interference with the vessel wall and potentially decreasing the access into the left common carotid artery. In some embodiments, the diameter of the rotation orb for a distal sheath is less than about 25 mm.

Referring back to FIG. 12A, distal sheath 112, in some embodiments, includes a non-steerable distal section 121, an intermediate steerable section 119, and a proximal non-steerable section 117. When the distal sheath is actuated to be steered, only steerable portion 119 bends into a different configuration. That is, the non-steerable portions retain substantially straight configurations. The distal non-steerable portion remains straight, which can allow the distal filter to be advanced into a proper position in the left common carotid artery.

While FIG. 12A shows distal sheath 112 in a bent configuration, the distal sheath is also positioned within the lumen of the aorta. In this position, the distal sheath can interfere with any other medical device or instrument that is being advanced through the aorta. For example, in aortic valve replacement procedures, delivery device 116, with a replacement aortic valve disposed therein, is delivered through the aorta as shown in FIG. 12B. If components of the filter system are disposed within the aorta during this time, delivery device 116 and the filter system can hit each other, potentially damaging either or both systems. The delivery device 116 can also dislodge one or both filters if they are in the expanded configurations. The filter system can additionally prevent the delivery device 116 from being advanced through the aorta. To reduce the risk of contact between delivery device 116 and distal sheath 112, distal sheath 112 (and distal shaft 110) is translated in the proximal direction relative to the proximal filter (which in this embodiment has already been expanded but is not shown), as is shown in FIG. 12B. Distal sheath 112 is pulled back until the inner curvature of distal sheath 112 is seated snugly with the vasculature 15 disposed between the brachiocephalic trunk 111 and the left common carotid artery 113. This additional seating step helps secure the distal sheath in place within the subject, as well as minimize the amount of the filter system present in the aortic arch. This additional seating step can be incorporated into any of the methods described herein, and is an exemplary advantage of having a distal sheath that has three degrees of independent motion relative to the proximal filter. The combination of independent rotation, steering, and axial translation can be clinically significant to ensure the distal filter is properly positioned in the lumen, as well as making sure the filter system does not interfere with any other medical devices being delivered to the general area inside the subject.

An additional advantage of the filter systems herein is that the distal sheath, when in the position shown in FIG. 11C, will act as a protection element against any other medical instruments being delivered through the aorta (e.g., delivery device 116). Even if delivery device 116 were advanced such that it did engage distal sheath 112, distal sheath 112 is seated securely against tissue 15, thus preventing distal sheath 112 from being dislodged. Additionally, distal sheath 112 is stronger than, for example, a wire positioned within the aorta, which can easily be dislodged when hit by delivery device 16.

Figure 15A:
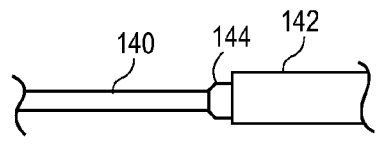
FIGS. 15A-15D illustrate alternative embodiments of the coupling of the distal shaft and distal sheath.
Figure 15B:
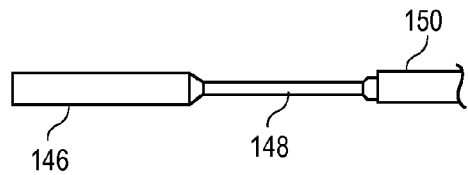
Figure 15C:
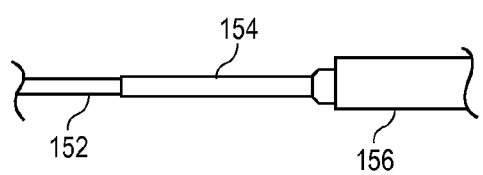
Figure 15D:
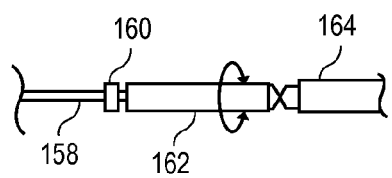

FIGS. 15A-15D illustrate alternative embodiments of the coupling of the distal shaft and distal sheath. In FIG. 15A distal shaft 140 is secured to distal sheath 142 by coupler 144. Shaft 140 has a low profile to allow for the collapse of the proximal filter (see FIG. 1C). Shaft 140 also has column strength to allow for axial translation, has sufficient torque transmission properties, and is flexible. The shaft can have a support structure therein, such as braided stainless steel. For example, the shaft can comprise polyimide, Polyether ether ketone (PEEK), Nylon, Pebax, etc. FIG. 15B illustrates an alternative embodiment showing tubular element 146, distal shaft 148, and distal sheath 150. Tubular element 146 can be a hypotube made from stainless steel, nitinol, etc. FIG. 15C illustrates an exemplary embodiment that includes distal shaft 152, traction member 154, and distal sheath 156. Traction member 154 is coupled to shaft 152 and shaft 152 is disposed therein. Traction member 154 couples to shaft 152 for torquebility, deliverability, and deployment. Traction member 154 can be, for example without limitation, a soft silicone material, polyurethane, or texture (e.g., polyimide, braid, etc.). FIG. 15D shows an alternative embodiment in which the system includes bushing 162 disposed over distal shaft 158, wherein distal shaft 158 is adapted to rotate within bushing 162. The system also includes stop 160 secured to distal shaft 158 to substantially maintain the axial position of bushing 162. When the system includes bushing 162, distal sheath 164 can be rotated relative to the proximal sheath and the proximal filter when the distal sheath and proximal sheath are in the delivery configuration (see FIG. 1B).

Figure 16:
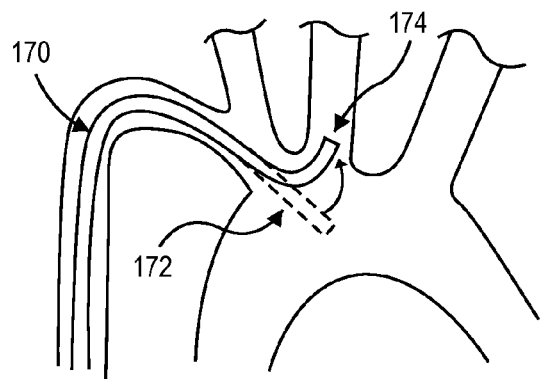
FIG. 16 illustrates an exemplary embodiment of a filter system in which the distal sheath is biased to a curved configuration.

FIG. 16 illustrates an exemplary embodiment of filter system 170 in which distal sheath 172 is biased to a curved configuration 174. The biased curved configuration is adapted to facilitate placement, delivery, and securing at least the distal filter. As shown, the distal sheath is biased to a configuration that positions the distal end of the distal sheath towards the left common carotid artery.

Figure 17:
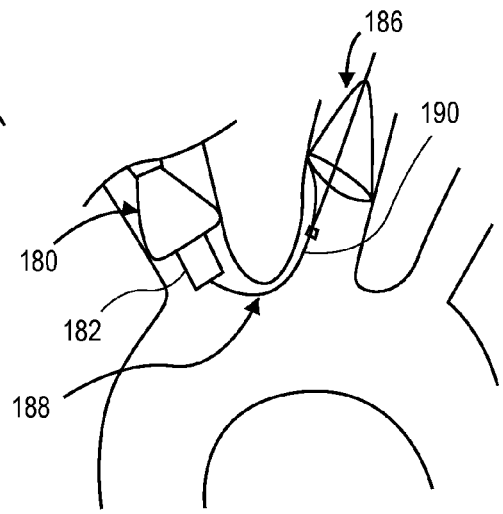
FIG. 17 illustrates a portion of an alternative filter system.

FIG. 17 illustrates a portion of an exemplary filter system and its method of use. FIG. 17 shows a system and portion of deployment similar to that shown in FIG. 2D, but distal sheath 182 has been retracted proximally relative to guiding member 190 and distal filter 186. Distal sheath 182 has been retracted substantially from the aortic arch and is substantially disposed with the brachiocephalic trunk. Guiding member 190 can have preset curve 188 adapted to closely mimic the anatomical curve between the brachiocephalic trunk and the left common carotid artery, thus minimizing the amount of the system that is disposed within the aorta. As shown, distal sheath 182 has been retracted proximally relative to proximal filter 180.

Figure 18A:
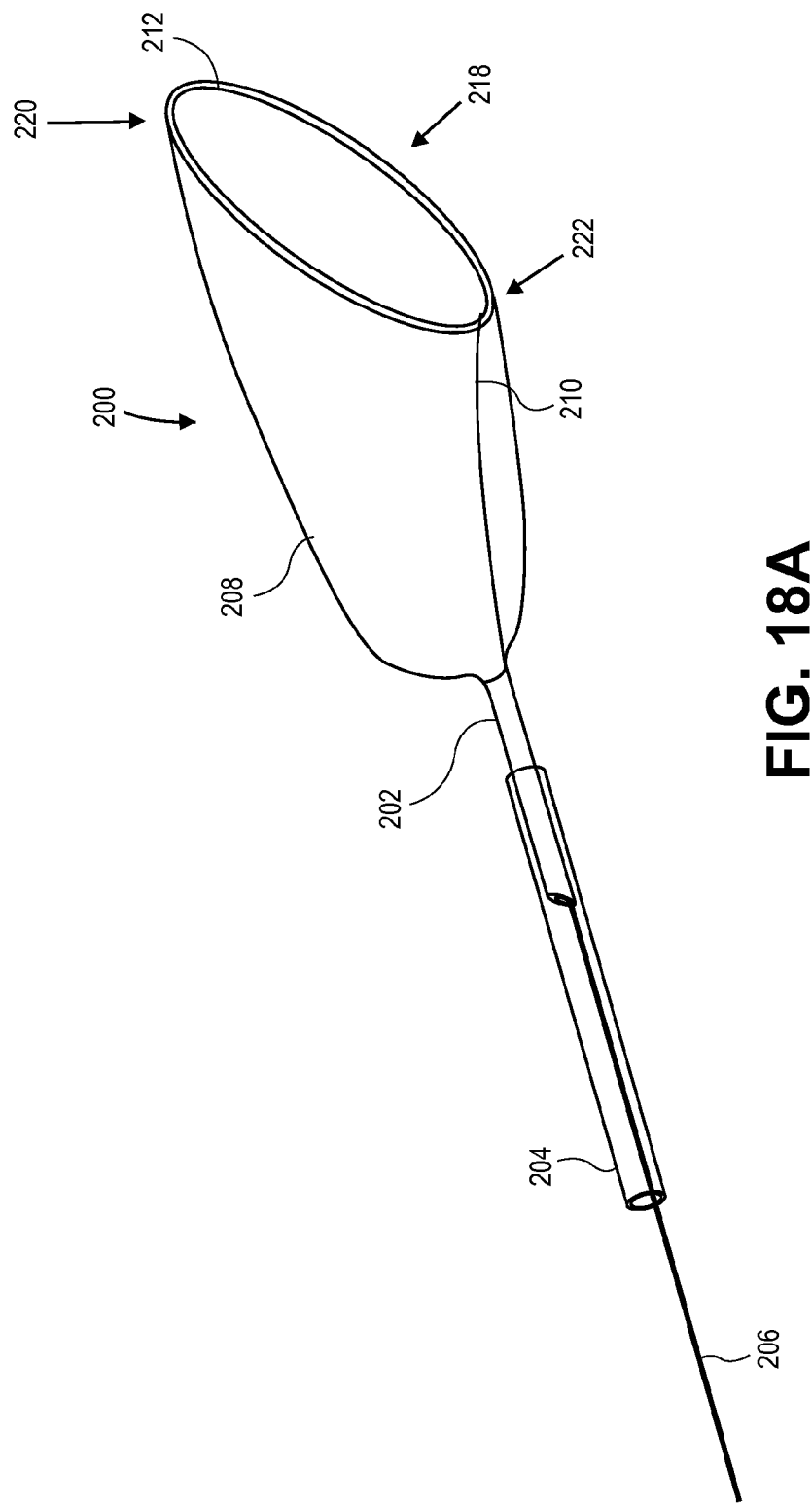
FIGS. 18A and 18B illustrate an exemplary proximal filter.
Figure 18B:
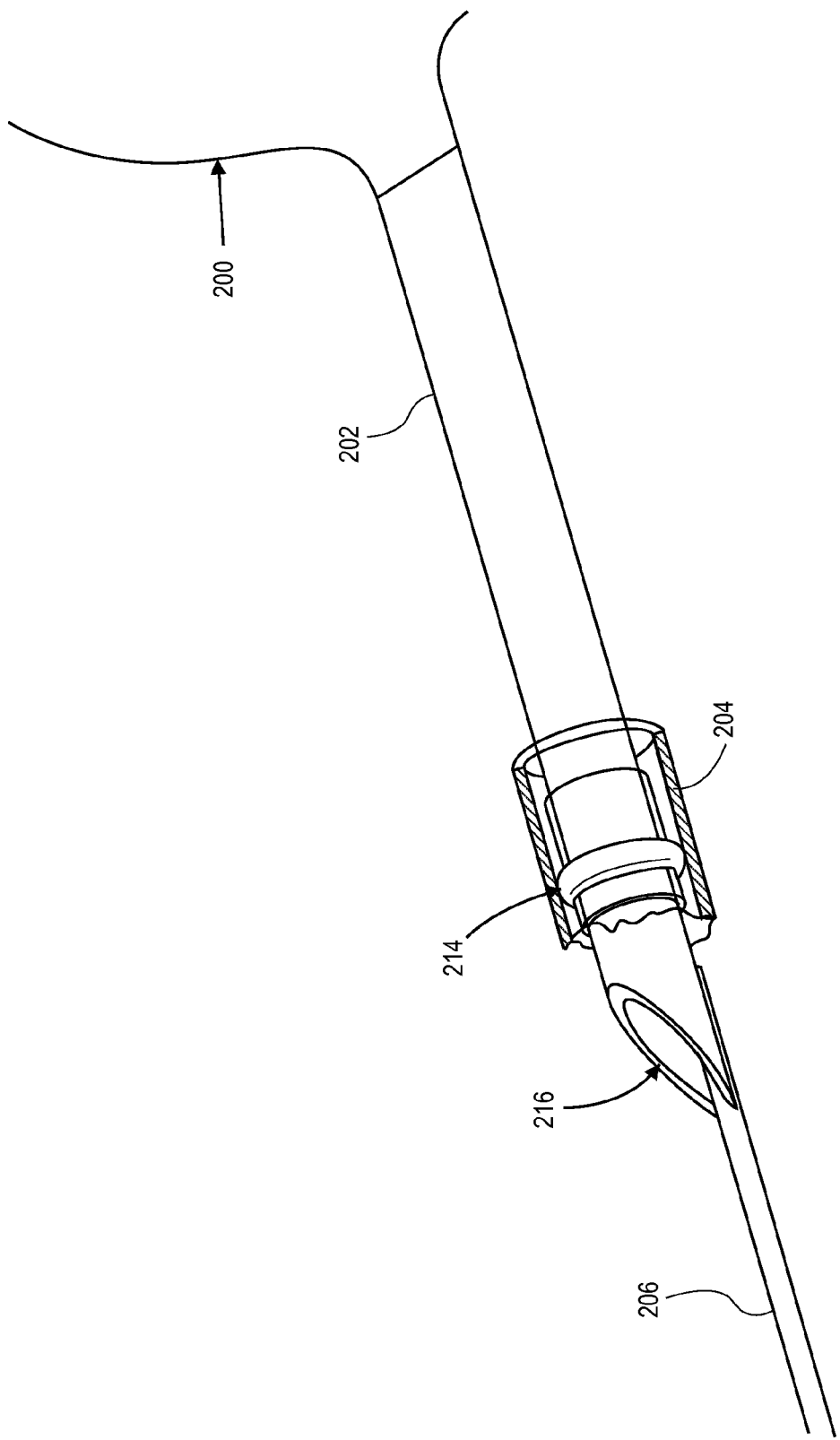

FIG. 18A is a perspective view of a portion of an exemplary embodiment of a filter system, while FIG. 18B is a close-up view of a portion of the system shown in FIG. 18A. The distal sheath and the distal filter are not shown in FIGS. 18A and 18B for clarity. The system includes proximal filter 200 coupled to proximal shaft 202, and push rod 206 coupled to proximal shaft 202. A portion of proximal sheath 204 is shown in FIG. 18A in a retracted position, allowing proximal filter 200 to expand to an expanded configuration. Only a portion of proximal sheath 204 is shown, but it generally extends proximally similar to push rod 206. The proximal end of proximal shaft 202 is beveled and defines an aspiration lumen 216, which is adapted to receive an aspirator (not shown) to apply a vacuum to aspirate debris captured within distally facing proximal filter 200. Push rod 206 extends proximally within proximal sheath 204 and is coupled to an actuation system outside of the subject, examples of which are described below. Push rod 206 takes up less space inside proximal sheath 204 than proximal shaft 202, providing a lower profile.

The system also includes proximal seal 214 disposed on the outer surface of proximal shaft 202 and adapted to engage the inner surface of the proximal sheath. Proximal seal 214 prevents bodily fluids, such as blood, from entering the space between proximal sheath 204 and proximal shaft 202, thus preventing bodily fluids from passing proximally into the filter system. The proximal seal can be, for example without limitation, a molded polymer. The proximal seal can also be machined as part of the proximal shaft, such that they are not considered two separate components.

In some specific embodiments the push rod is about 0.015 inches in diameter, and is grade 304 stainless steel grade. The proximal shaft can be, for example without limitation, an extruded or molded plastic, a hypotube (e.g., stainless steel), machined plastic, metal, etc.

Proximal filter 200 includes filter material 208, which comprises pores adapted to allow blood to pass therethrough, while debris does not pass through the pores and is captured within the filter material. Proximal filter 200 also includes strut 210 that extends from proximal shaft 202 to expansion support 212. Expansion support 212 has a generally annular shape but that is not intended to be limiting. Proximal filter 200 also has a leading portion 220 and a trailing portion 222. Leading portion 220 generally extends further distally than trailing portion 222 to give filter 200 a generally canted configuration relative to the proximal shaft. The canted design provides for decreased radial stiffness and a better collapsed profile. Strut 210 and expansion support 212 generally provide support for filter 200 when in the expanded configuration, as shown in FIG. 18A.

Figure 19A:
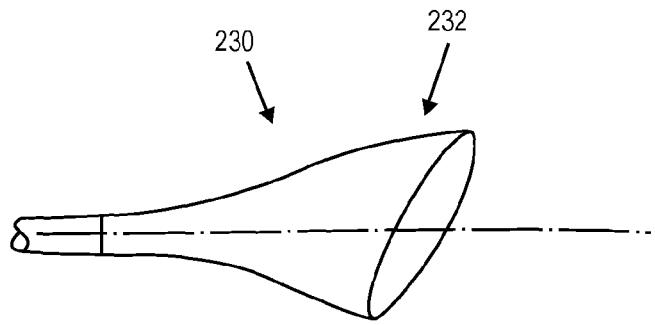
FIGS. 19A-22B illustrate exemplary proximal filters.
Figure 19B:
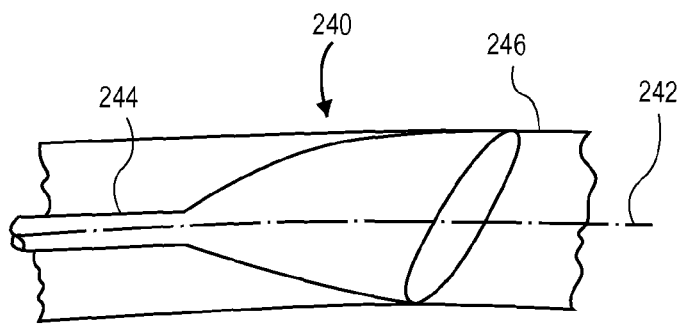
Figure 19C:
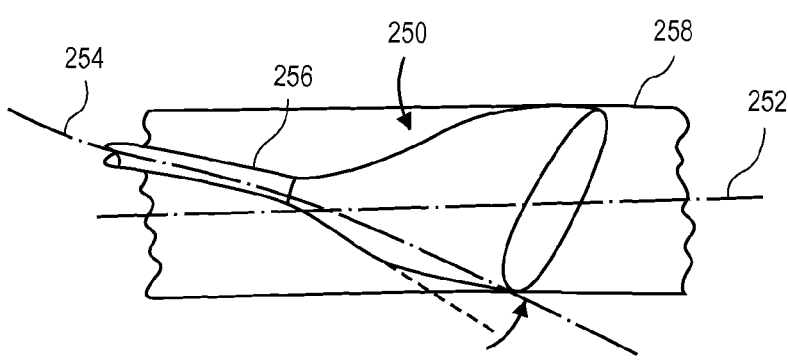

FIGS. 19A-19C illustrate exemplary embodiments of proximal filters and proximal shafts that can be incorporated into any of the systems herein. In FIG. 19A, filter 230 has flared end 232 for improved filter-wall opposition. FIG. 19B shows proximal shaft 244 substantially co-axial with vessel 246 in which filter 240 is expanded. Vessel 246 and shaft 244 have common axis 242. FIG. 19C illustrates longitudinal axis 254 of shaft 256 not co-axial with axis 252 of lumen 258 in which filter 250 is expanded.

Figure 20B:
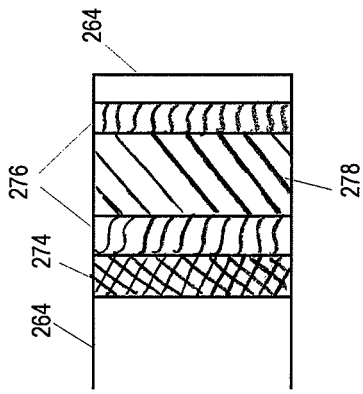
Figure 20A:
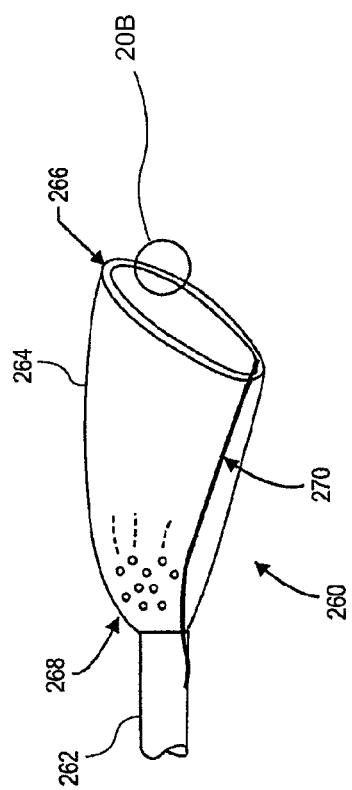

FIGS. 20A and 20B illustrate an exemplary embodiment including proximal filter 260 coupled to proximal shaft 262. Filter 260 includes filter material 264, including slack material region 268 adapted to allow the filter to collapse easier. Filter 260 is also shown with at least one strut 270 secured to shaft 262, and expansion support 266. As shown in the highlighted view in FIG. 20B, filter 260 includes seal 274, radiopaque coil 276 (e.g., platinum), and support wire 278 (e.g., nitinol wire). Any of the features in this embodiment can be included in any of the filter systems described herein.

Figure 21:
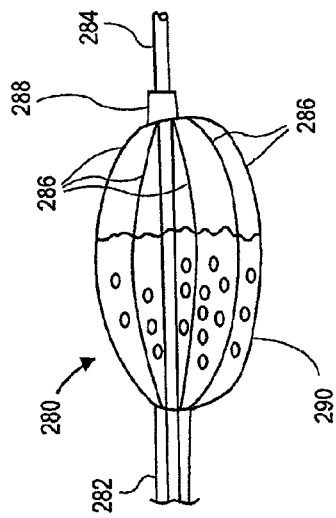

FIG. 21 illustrates an exemplary embodiment of a proximal filter. Proximal filter 280 is coupled to proximal shaft 282. Proximal filter 280 includes struts 286 extending from proximal shaft 282 to strut restraint 288, which is adapted to slide axially over distal shaft 284. Proximal filter 280 also includes filter material 290, with pores therein, that extends from proximal shaft 282 to a location axially between proximal shaft 282 and strut restraint 288. Debris can pass through struts 286 and become trapped within filter material 290. When proximal filter 280 is collapsed within a proximal sheath (not shown), struts 286 elongate and move radially inward (towards distal shaft 284). Strut restraint 288 is adapted to move distally over distal shaft 284 to allow the struts to move radially inward and extend a greater length along distal shaft 284.

Figure 22A:
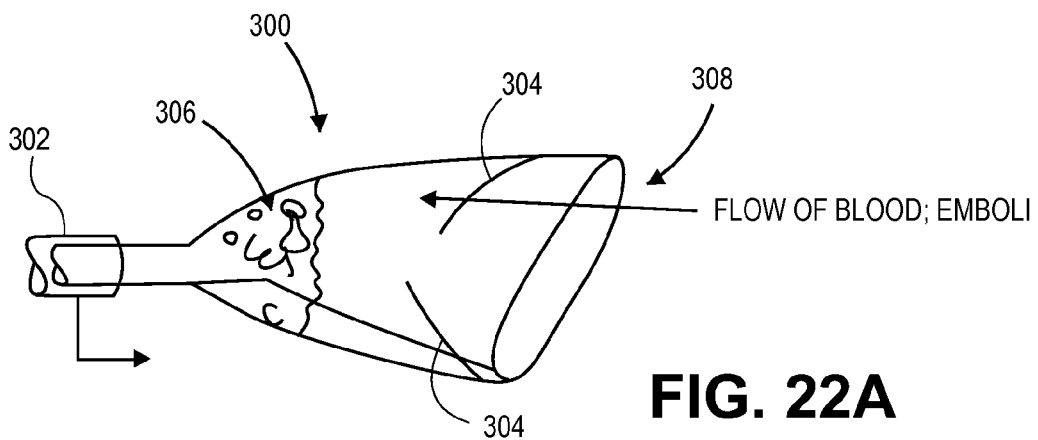
Figure 22B:
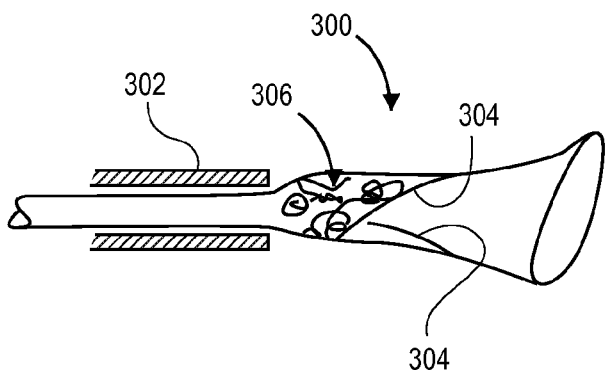

FIGS. 22A and 22B illustrate an exemplary embodiment of a proximal filter that can be incorporated into any filter system described herein. The system includes proximal filter 300 and proximal sheath 302, shown in a retracted position in FIG. 22A. Proximal filter 300 includes valve elements 304 in an open configuration in FIG. 22A. When valve elements 304 are in the open configuration, foreign particles 306 can pass through opening 308 and through the valve and become trapped in proximal filter 300, as is shown in FIG. 22A. To collapse proximal filter 300, proximal sheath 302 is advanced distally relative to proximal filter 300. As the filter begins to collapse, the valve elements are brought closer towards one another and into a closed configuration, as shown in FIG. 22B. The closed valve prevents extrusion of debris during the recapture process.

The distal filters shown are merely exemplary and other filters may be incorporated into any of the systems herein. FIG. 23A illustrates a portion of an exemplary filter system. The system includes guiding member 340 (distal sheath not shown), strut 342, expansion support 344, and filter element 346. Strut 342 is secured directly to guiding member 340 and strut 342 is secured either directly or indirectly to expansion support 344. Filter material 346 is secured to expansion support 344. Distal end 348 of filter material 346 is secured to guiding member 340.

FIG. 23B illustrates a portion of an exemplary filter system. The system includes guiding element 350, strut support 352 secured to guiding element 350, strut 354, expansion support 356, and filter material 358. Strut support 352 can be secured to guiding element 350 in any suitable manner (e.g., bonding), and strut 354 can be secured to strut support 352 in any suitable manner.

FIG. 23C illustrates a portion of an exemplary filter system. The system includes guiding element 360, strut support 362 secured to guiding element 360, strut 364, expansion support 366, and filter material 368. Expansion support 366 is adapted to be disposed at an angle relative to the longitudinal axis of guiding member 360 when the distal filter is in the expanded configuration. Expansion support 366 includes trailing portion 362 and leading portion 361. Strut 364 is secured to expansion support 366 at or near leading portion 361. FIG. 23D illustrates an exemplary embodiment that includes guiding member 370, strut support 372, strut 374, expansion support 376, and filter material 378. Expansion support 376 includes leading portion 373, and trailing portion 371, wherein strut 374 is secured to expansion element 376 at or near trailing portion 371. Expansion support 376 is disposed at an angle relative to the longitudinal axis of guiding member 370 when the distal filter is in the expanded configuration.

FIG. 23E illustrates an exemplary embodiment of a distal filter in an expanded configuration. Guiding member 380 is secured to strut support 382, and the filter includes a plurality of struts 384 secured to strut support 382 and to expansion support 386. Filter material 388 is secured to expansion support 386. While four struts are shown, the distal filter may include any number of struts.

FIG. 23F illustrates an exemplary embodiment of a distal filter in an expanded configuration. Proximal stop 392 and distal stop 394 are secured to guiding member 390. The distal filter includes tubular member 396 that is axially slideable over guiding member 390, but is restricted in both directions by stops 392 and 394. Strut 398 is secured to slideable member 396 and to expansion support 393. Filter material 395 is secured to slideable member 396. If member 396 slides axially relative to guiding member 390, filter material 395 moves as well. Member 396 is also adapted to rotate in the direction "R" relative to guiding member 390. The distal filter is therefore adapted to independently move axially and rotationally, limited in axial translation by stops 392 and 394. The distal filter is therefore adapted such that bumping of the guiding member or the distal sheath will not disrupt the distal filter opposition, positioning, or effectiveness.

FIGS. 24A-24C illustrate exemplary embodiments in which the system includes at least one distal filter positioning, or stabilizing, anchor. The positioning anchor(s) can help position the distal anchor in a proper position and/or orientation within a bodily lumen. In FIG. 24A the system includes distal filter 400 and positioning anchor 402. Anchor 402 includes expandable stent 404 and expandable supports 406. Supports 406 and filter 400 are both secured to the guiding member. Anchor 402 can be any suitable type of expandable anchor, such as, for example without limitation, stent 404. Anchor 402 can be self-expandable, expandable by an expansion mechanism, or a combination thereof. In FIG. 24A, stent 404 can alternatively be expanded by an expansion balloon. Anchor 402 is disposed proximal to filter 400. FIG. 24B illustrates an embodiment in which the system includes first and second anchors 412 and 414, one of which is proximal to filter 410, while the other is distal to filter 410. FIG. 24C illustrates an embodiment in which anchor 422 is distal relative to filter 420.

In some embodiments the distal filter is coupled, or secured, to a guiding member that has already been advanced to a location within the subject. The distal filter is therefore coupled to the guiding member after the distal filter has been advanced into the subject, rather than when the filter is outside of the subject. Once coupled together inside the subject, the guiding member can be moved (e.g., axially translated) to control the movement of the distal filter. In some embodiments the guiding member has a first locking element adapted to engage a second locking element on the distal filter assembly such that movement of the guiding member moves the distal filter in a first direction. In some embodiments the distal filter assembly has a third locking element that is adapted to engage the first locking element of the guiding member such that movement of the guiding member in a second direction causes the distal filter to move with the guiding member in the second direction. The guiding member can therefore be locked to the distal filter such that movement of the guiding member in a first and a second direction will move the distal filter in the first and second directions.

By way of example, FIGS. 25A-25D illustrate an exemplary embodiment of coupling the distal filter to a docking wire inside of the subject, wherein the docking wire is subsequently used to control the movement of the distal filter relative to the distal sheath. In FIG. 25A, guide catheter 440 has been advanced through the subject until the distal end is in or near the brachiocephalic trunk 441. A docking wire, comprising a wire 445, locking element 442, and tip 444, has been advanced through guide catheter 440, either alone, or optionally after guiding wire 446 has been advanced into position. Guiding wire 446 can be used to assist in advancing the docking wire through guide catheter 440. As shown, the docking wire has been advanced from the distal end of guide catheter 440. After the docking wire is advanced to the desired position, guide catheter 440, and if guiding wire 446 is used, are removed from the subject, leaving the docking wire in place within the subject, as shown in FIG. 25B. Next, as shown in FIG. 25C, the filter system, including proximal sheath 448 with a proximal filter in a collapsed configuration therein (not shown), distal sheath 450, with a distal filter assembly (not shown) partially disposed therein, is advanced over wire 445 until a locking portion of the distal filter (not shown but described in detail below) engages locking element 442. The distal filter assembly will thereafter move (e.g., axially) with the docking wire. Proximal sheath 448 is retracted to allow proximal filter 454 to expand (see FIG. 25D). Distal sheath 450 is then actuated (e.g., bent, rotated, and/or translated axially) until it is in the position shown in FIG. 25D. A straightened configuration of the distal sheath is shown in phantom in FIG. 25D, prior to bending, proximal movement, and/or bending. The docking wire is then advanced distally relative to distal sheath 450, which advances distal filter 456 from distal sheath 450, allowing distal filter 456 to expand inside the left common carotid artery, as shown in FIG. 25D.

Figure 26A:
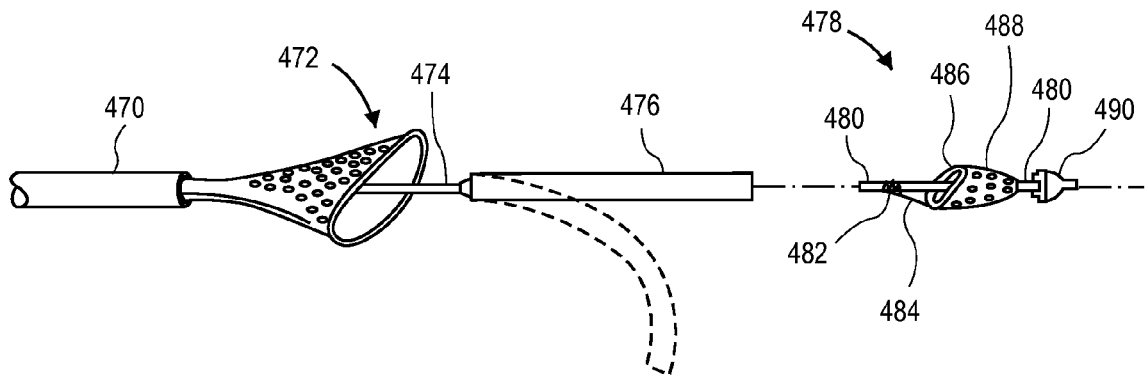
FIGS. 26A-26G illustrate an exemplary method of preparing an exemplary distal filter assembly for use.
Figure 26B:
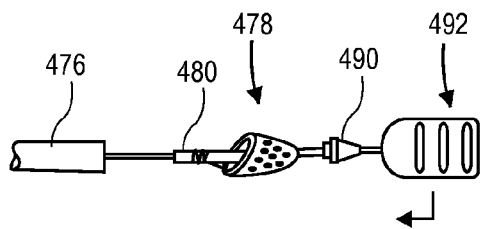
Figure 26C:
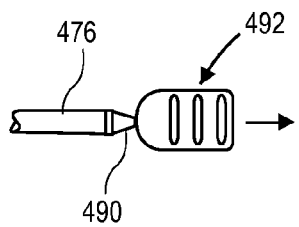
Figure 26D:
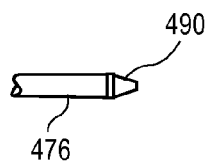

FIGS. 26A-26D illustrate an exemplary method of preparing an exemplary distal filter assembly for use. FIG. 26A illustrates a portion of the filter system including proximal sheath 470, proximal filter 472 is an expanded configuration, distal shaft 474, and articulatable distal sheath 476. Distal filter assembly 478 includes an elongate member 480 defining a lumen therein. Elongate member 480 is coupled to distal tip 490. Strut 484 is secured both to strut support 482, which is secured to elongate member 480, and expansion support 486. Filter element 488 has pores therein and is secured to expansion support 486 and elongate member 480. To load distal filter assembly 478 into distal sheath 476, loading mandrel 492 is advanced through distal tip 490 and elongate member 480 and pushed against distal tip 490 until distal filter assembly 478 is disposed within distal sheath 476, as shown in FIG. 26C. Distal tip 490 of the filter assembly remains substantially distal to distal sheath 476, and is secured to the distal end of distal sheath 476. Distal tip 490 and distal sheath 476 can be secured together by a frictional fit or other type of suitable fit that disengages as described below. Loading mandrel 492 is then removed from the distal filter and distal sheath assembly, as shown in FIG. 26D.

Figure 26E:
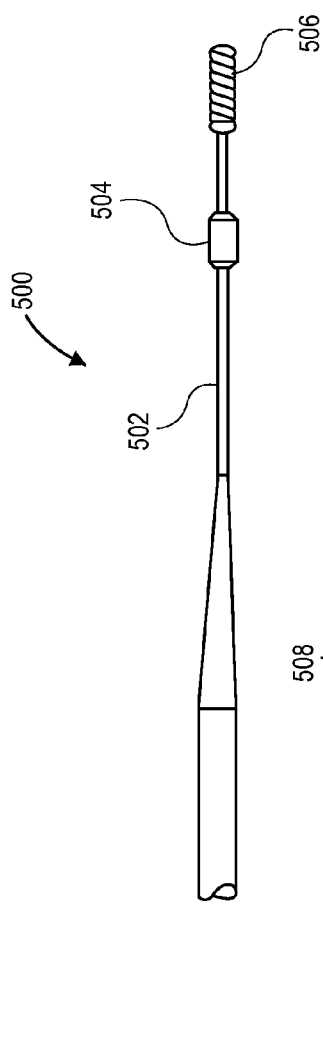
Figure 26F:
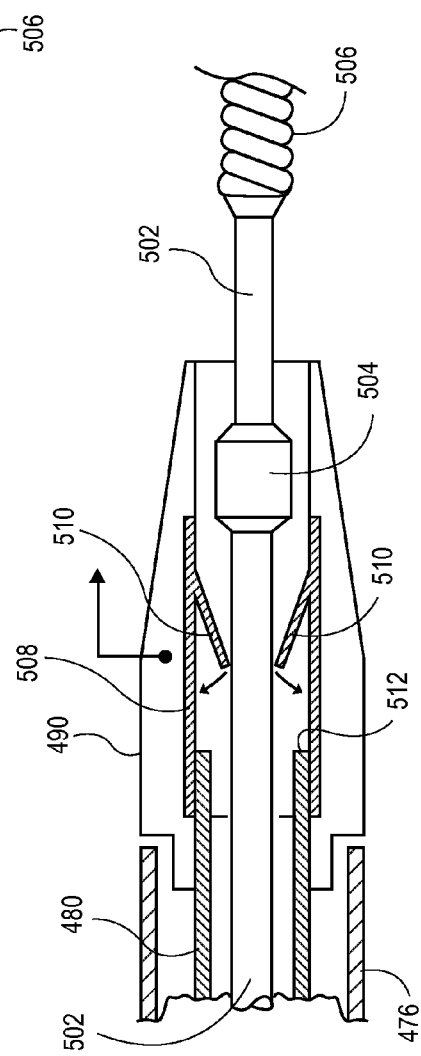
Figure 26G:
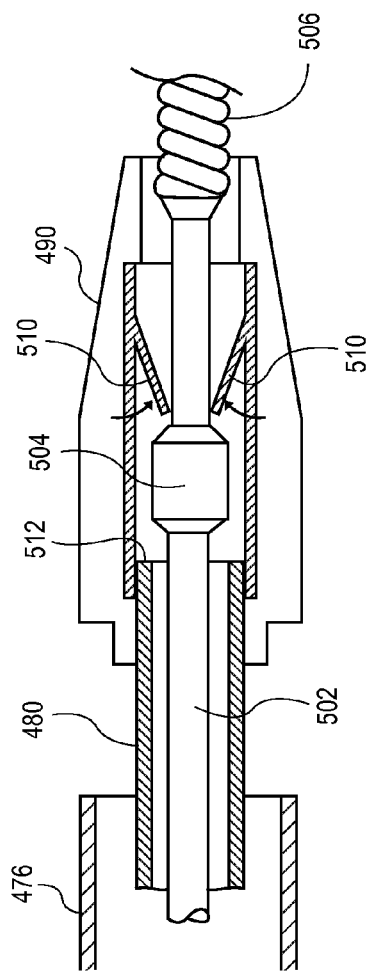

FIG. 26E illustrates docking wire 500 including wire 502, lock element 504, and distal tip 506. Docking wire 500 is first advanced to a desired position within the subject, such as is shown in FIG. 25B. The assembly from FIG. 26D is then advanced over docking wire, wherein distal tip 490 is first advanced over the docking wire. As shown in the highlighted view in FIG. 26F, distal tip 490 of the distal filter assembly includes first locking elements 510, shown as barbs. As the filter/sheath assembly continues to be distally advanced relative to the docking wire, the docking wire locking element 504 pushes locks 510 outward in the direction of the arrows in FIG. 26F. After lock 504 passes locks 510, locks 510 spring back inwards in the direction of the arrows shown in FIG. 26G. In this position, when docking wire 500 is advanced distally (shown in FIG. 26F), lock element 504 engages with lock elements 510, and the lock element 504 pushes the distal filter assembly in the distal direction. In this manner the distal filter can be distally advanced relative to the distal sheath to expand the distal filter. Additionally, when the docking wire is retracted proximally, locking element 504 engages the distal end 512 of elongate member 480 and pulls the distal filter in the proximal direction. This is done to retrieve and/or recollapse the distal filter back into the distal sheath after it has been expanded.

FIGS. 27A and 27B illustrate an exemplary embodiment in which guiding member 540, secured to distal filter 530 before introduction into the subject is loaded into articulatable distal sheath 524. The system also includes proximal filter 520, proximal sheath 522, and distal shaft 526. FIG. 27B shows the system in a delivery configuration in which both filters are collapsed.

Figure 28A:
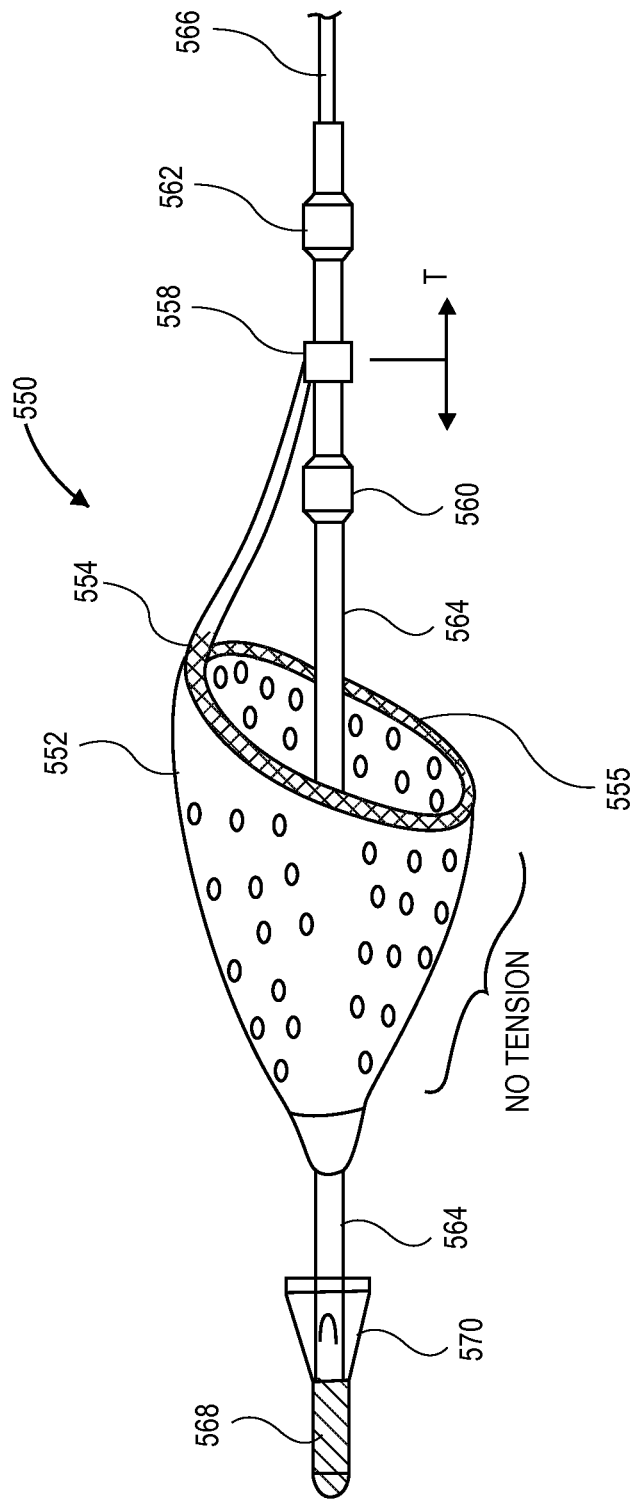
FIGS. 28A-28E illustrate an exemplary distal filter assembly in collapsed and expanded configurations.

FIGS. 28A-28E illustrate an exemplary distal filter assembly in collapsed and expanded configurations. In FIG. 28A, distal filter assembly 550 includes a distal frame, which includes strut 554 and expansion support 555. The distal frame is secured to floating anchor 558, which is adapted to slide axially on elongate member 564 between distal stop 560 and proximal stop 562, as illustrated by the arrows in FIG. 28A. The distal filter assembly also includes membrane 552, which has pores therein and is secured at its distal end to elongate member 564. The distal filter assembly is secured to a guiding member, which includes wire 566 and soft distal tip 568. The guiding member can be, for example, similar to the docking wire shown in FIGS. 26A-26E above, and can be secured to the distal filter assembly as described in that embodiment.

The floating anchor 558 allows filter membrane 552 to return to a neutral, or at-rest, state when expanded, as shown in FIG. 28A. In its neutral state, there is substantially no tension applied to the filter membrane. The neutral deployed state allows for optimal filter frame orientation and vessel apposition. In the neutral state shown in FIG. 28A, floating anchor 558 is roughly mid-way between distal stop 560 and proximal stop 562, but this is not intended to be a limiting position when the distal filter is in a neutral state.

Figure 28B:
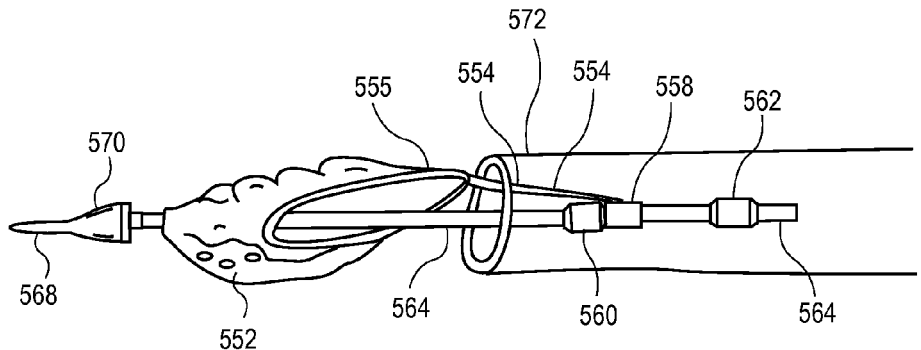
Figure 28C:
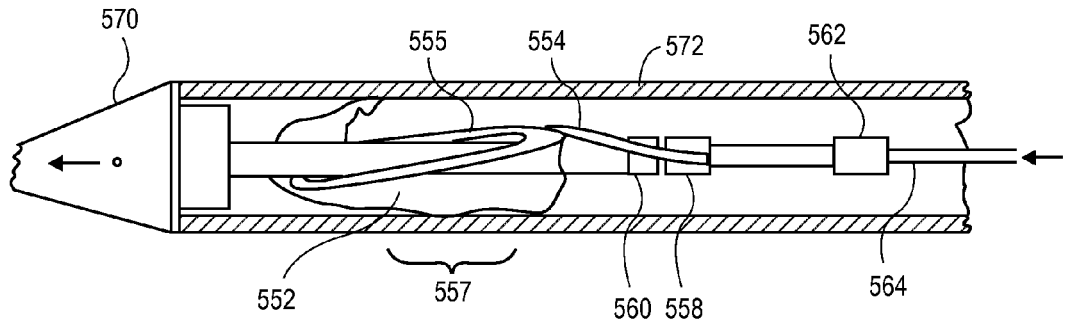
Figure 28D:
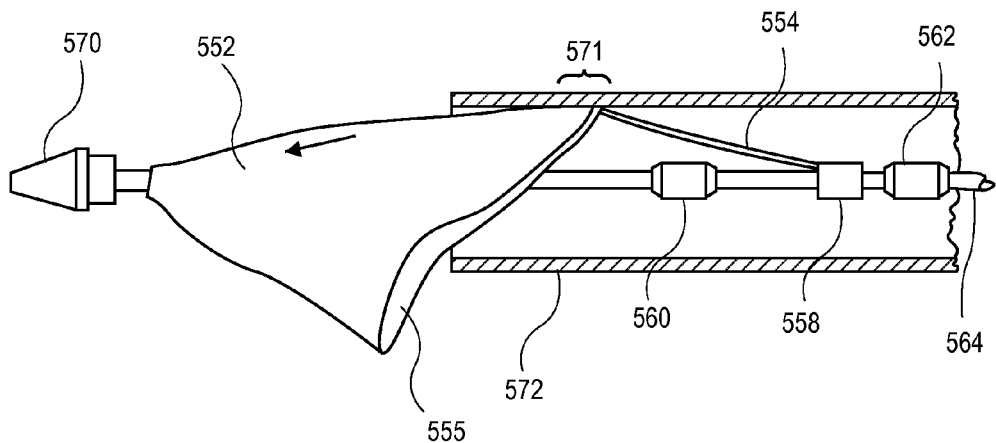
Figure 28E:
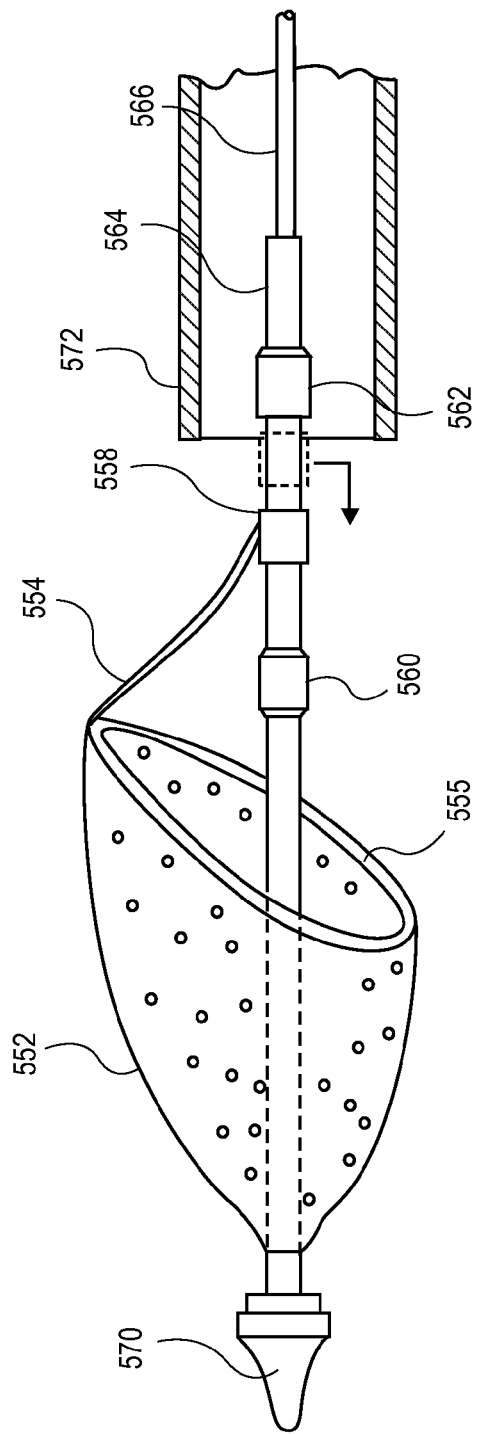

FIG. 28B illustrates the distal filter being sheathed into distal sheath 572. During the sheathing process, the distal filter is collapsed from an expanded configuration (see FIG. 28A) towards a collapsed configuration (see FIG. 28C). In FIG. 28B, distal sheath 572 is moving distally relative to the distal filter. The distal end of the distal sheath 572 engages with strut 554 as it is advanced distally, causing the distal end of strut 554 to moves towards elongate member 564. Strut 554 can be thought of as collapsing towards elongate member 564 from the configuration shown in FIG. 28A. The force applied from distal sheath 572 to strut 554 collapses the strut, and at the same time causes floating anchor 558 to move distally on tubular member 564 towards distal stop 560. In FIG. 28B, floating anchor 558 has been moved distally and is engaging distal stop 560, preventing any further distal movement of floating anchor 558. As strut 554 is collapsed by distal sheath 572, strut 554 will force the attachment point between strut 554 and expansion support 555 towards tubular member 564, beginning the collapse of expansion support 555. Distal sheath 172 continues to be advanced distally relative to the distal filter (or the distal filter is pulled proximally relative to the distal sheath, or a combination of both) until the distal filter is collapsed within distal sheath 172, as is shown in FIG. 28C. Filter membrane 552 is bunched to some degree when the filter is in the configuration shown in FIG. 28C. To deploy the distal filter from the sheath, guiding member 566 is advanced distally relative to the distal sheath (or the distal sheath is moved proximally relative to the filter). The distal portions of filter membrane 552 and expansion support 555 are deployed first, as is shown in FIG. 28D. Tension in the filter membrane prevents wadding and binding during the deployment. When strut 554 is deployed from the distal sheath, expansion support 555 and strut 554 are able to self-expand to an at-rest configuration, as shown in FIG. 28E. Floating anchor 558 is pulled in the distal direction from the position shown in FIG. 28D to the position shown in FIG. 28E due to the expansion of strut 554.

FIGS. 29A-29E illustrate a portion of an exemplary filter system with a lower delivery and insertion profile. In FIG. 29A, the system includes proximal sheath 604 with a larger outer diameter than distal sheath 602. In some embodiments proximal sheath 604 has a 6 F outer diameter, while distal sheath 602 has a 5 F outer diameter. A guiding member including distal tip 606 is disposed within the distal sheath and the proximal sheath. FIG. 29B illustrates tear-away introducer 608, with receiving opening 610 and distal end 612. Introducer is first positioned within a subject with receiving opening 610 remaining outside the patient. As shown in FIG. 29C, the smaller diameter distal sheath is first advanced through the receiving opening of introducer 608 until the distal end of the distal sheath is disposed distal relative to the distal end of the introducer. The introducer is then split apart and removed from the subject, as shown in FIG. 29D. The filter system can then be advanced distally through the subject. The introducer can be a 5 F introducer, which reduces the insertion and delivery profile of the system.

The embodiments in FIGS. 25A-25B above illustrated some exemplary systems and methods for routing filter systems to a desired location within a subject, and additional exemplary embodiments will now be described. FIGS. 30A and 30B illustrate an exemplary embodiment similar to that which is shown in FIGS. 27A and 27B. The filter system shows distal filter 650 and proximal filter 644 in expanded configurations. Proximal sheath 642 has been retracted to allow proximal filter 644 to expand. Distal filter, which is secured to guiding member 648, are both advanced distally relative to distal articulating sheath 640. The filter system does not have a dedicated guidewire that is part of the system, but distal sheath 640 is adapted to be rotated and steered to guide the system to a target location within the subject.

FIGS. 31A-31C illustrate an exemplary over-the-wire routing system that includes a separate distal port for a dedicated guidewire. A portion of the system is shown in FIG. 31B, including distal articulating sheath 662 and proximal sheath 660 (the filters are collapsed therein). FIG. 31A is a highlighted view of a distal region of FIG. 31B, showing guidewire entry port 666 near the distal end 664 of distal sheath 662. FIG. 31C is a sectional view through plane A of distal sheath 662, showing guidewire lumen 672, spine element 678, distal filter lumen 674, and steering element 676 (shown as a pullwire). Guidewire lumen 672 and distal filter lumen 674 are bi-axial along a portion of distal sheath, but in region 670 guidewire lumen 672 transitions from within the wall of distal sheath 662 to being co-axial with proximal sheath 660.

To deliver the system partially shown in FIGS. 31A-31C, a guidewire is first delivered to a target location within the subject. The guidewire can be any type of guidewire, such as a 0.014 inch coronary wire. With the guidewire in position, the proximal end of the guidewire is loaded into guidewire entry port 666. The filter system is then tracked over the guidewire to a desired position within the subject. Once the system is in place, the guidewire is withdrawn from the subject, or it can be left in place. The proximal and distal filters can then be deployed as described in any of the embodiments herein.

Figure 32A:
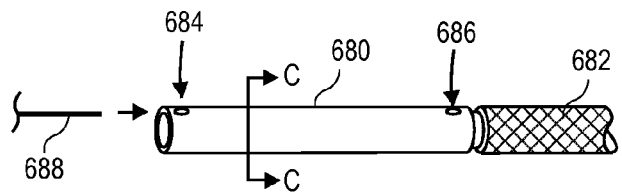
FIGS. 32A-32E illustrate an exemplary routing system which includes a rapid-exchange guidewire delivery.
Figure 32B:
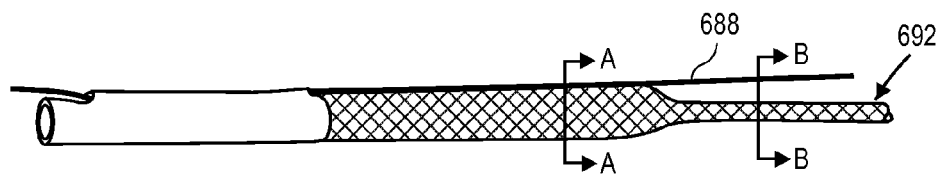
Figure 32C:
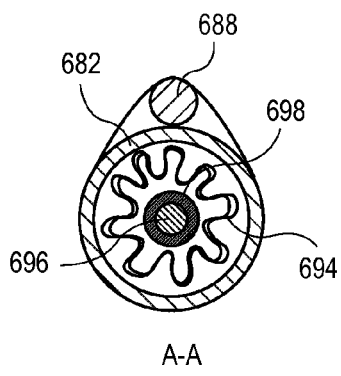
Figure 32D:
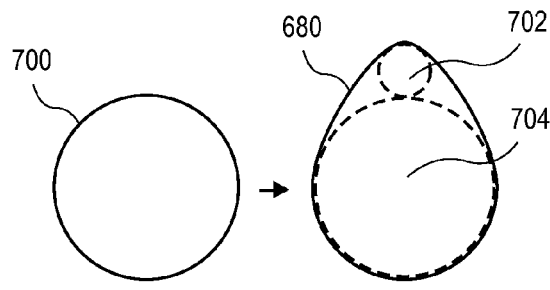
Figure 32E:
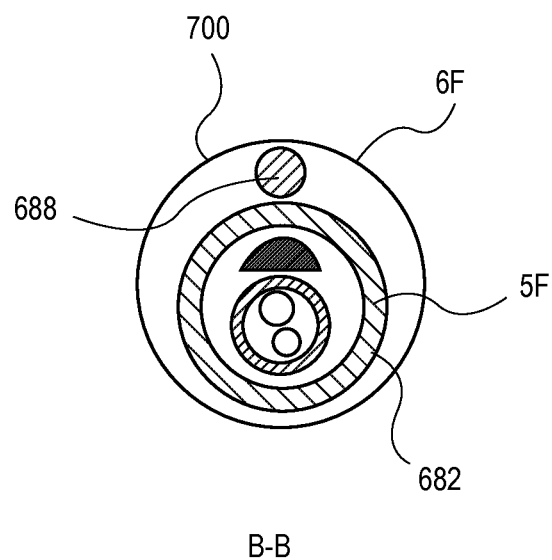

FIGS. 32A-32E illustrate an exemplary routing system which includes a rapid-exchange guidewire delivery. The system includes distal articulating sheath 680 with guidewire entry port 684 and guidewire exit port 686. The system also includes proximal sheath 682, a distal filter secured to a guiding member (collapsed within distal sheath 680), and a proximal filter (collapsed within proximal sheath 682). After guidewire 688 is advanced into position within the patient, the proximal end of guidewire 688 is advanced into guidewire entry port 684. Distal sheath (along with the proximal sheath) is tracked over guidewire 688 until guidewire 688 exits distal sheath 680 at guidewire exit port 686. Including a guidewire exit port near the entry port allows for only a portion of the guidewire to be within the sheath(s), eliminating the need to have a long segment of guidewire extending proximally from the subject's entry point. As soon as the guidewire exits the exit port, the proximal end of the guidewire and the proximal sheath can both be handled. FIG. 32B shows guidewire 688 extending through the guidewire lumen in the distal sheath and extending proximally from exit port 686. Guidewire 688 extends adjacent proximal sheath 682 proximal to exit port 686. In FIG. 32B, portion 690 of proximal sheath 682 has a diameter larger than portion 692 to accommodate the proximal filter therein. Portion 692 has a smaller diameter for easier passage of the proximal sheath and guidewire. FIG. 32C shows a sectional view through plane A, with guidewire 688 exterior and adjacent to proximal sheath 682. Proximal filter 694 is in a collapsed configuration within proximal sheath 682, and guiding member 696 is secured to a distal filter, both of which are disposed within distal shaft 698. FIG. 32D shows relative cross-sections of exemplary introducer 700, and distal sheath 680 through plane CC. Distal sheath 680 includes guidewire lumen 702 and distal filter lumen 704. In some embodiments, introducer 700 is 6 F, with an inner diameter of about 0.082 inches. In comparison, the distal sheath can have a guidewire lumen of about 0.014 inches and distal filter lumen diameter of about 0.077 inches. In these exemplary embodiments, as the distal sheath is being advanced through an introducer sheath, the introducer sheath can tent due to the size and shape of the distal sheath. There may be some slight resistance to the advancement of the distal sheath through the introducer sheath. FIG. 32E shows a sectional view through plane B, and also illustrates the insertion through introducer 700. Due to the smaller diameter of portion 692 of proximal sheath 682, guidewire 688 and proximal sheath 682 more easily fit through introducer 700 than the distal sheath and portion of the proximal sheath distal to portion 692. Introducer is 6 F, while proximal sheath is 5 F. Guidewire 688 is a 0.014 inch diameter guidewire. The smaller diameter proximal portion 692 of proximal sheath 682 allows for optimal sheath and guidewire movement with the introducer sheath.

Figure 33:
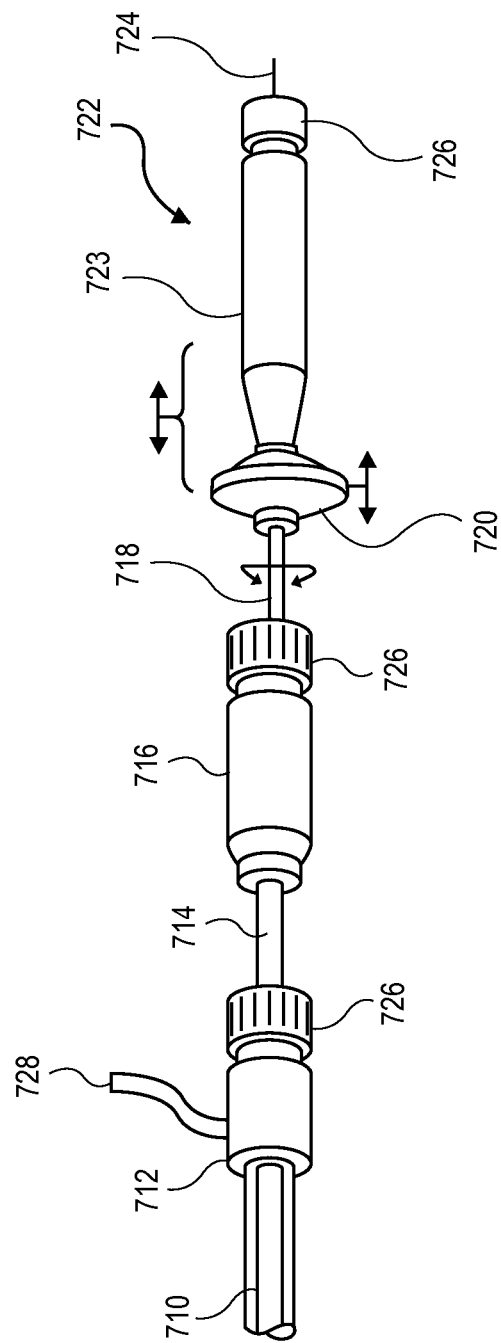
FIGS. 33-35 illustrate exemplary handle portions of the blood filter systems.

FIG. 33 illustrates a portion of an exemplary filter system. The portion shown in FIG. 33 is generally the portion of the system that remains external to the subject and is used to control the delivery and actuation of system components. Proximal sheath 710 is fixedly coupled to proximal sheath hub 712, which when advanced distally will sheath the proximal filter (as described herein), and when retracted proximally will allow the proximal filter to expand. The actuation, or control, portion also includes handle 716, which is secured to proximal shaft 714. When handle 716 is maintained axially in position, the position of the proximal filter is axially maintained. The actuation portion also includes distal sheath actuator 722, which includes handle 723 and deflection control 720. Distal sheath actuator 722 is secured to distal shaft 718. As described herein, the distal articulating sheath is adapted to have three independent degrees of motion relative to the proximal sheath and proximal filter: rotation, axially translation (i.e., proximal and distal), and deflection, and distal sheath actuator 722 is adapted to move distal sheath 718 in the three degrees of motion. Distal sheath 718 is rotated in the direction shown in FIG. 33 by rotating distal sheath actuator 722. Axial translation of distal sheath occurs by advancing actuator 722 distally (pushing) or by retracting actuator 722 proximally (pulling). Distal sheath 218 is deflected by axial movement of deflection control 720. Movement of deflection control 720 actuates the pullwire(s) within distal sheath 718 to control the bending of distal sheath 718. Also shown is guiding member 724, which is secured to the distal filter and is axially movable relative to the distal sheath to deploy and collapse the distal filter as described herein. The control portion also includes hemostasis valves 726, which is this embodiment are rotating.

Figure 34:
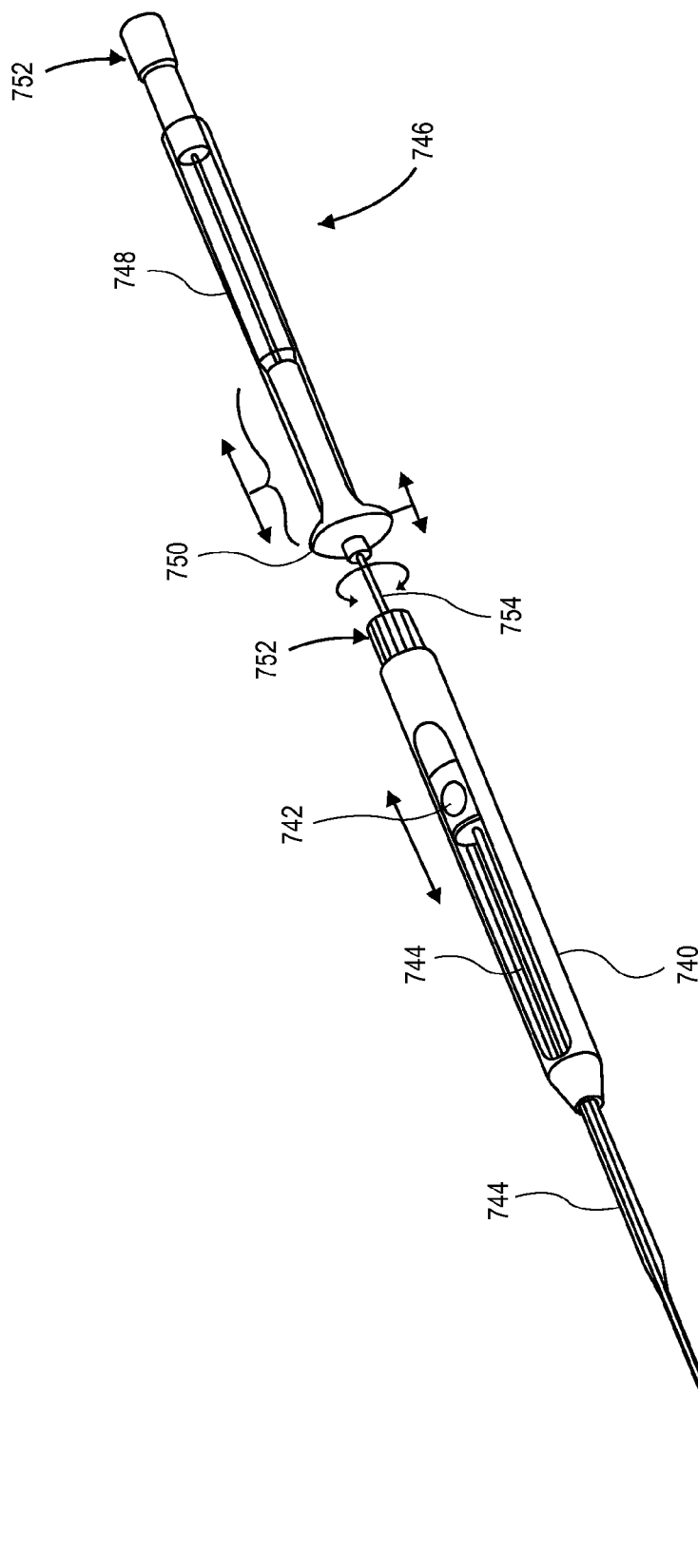

FIG. 34 illustrates an exemplary 2-piece handle design that can be used with any of the filter systems described herein. This 2-piece handle design includes distal sheath actuator 746, which includes handle section 748 and deflection control knob 750. Deflection control knob 750 of distal sheath actuator 746 is secured to distal shaft 754. Axial movement of distal sheath actuator 746 will translate distal shaft 754 either distally or proximally relative to the proximal filter and proximal sheath. A pull wire (not shown in FIG. 34) is secured to handle section 748 and to the distal articulatable sheath (not shown in FIG. 34). Axial movement of deflection control knob 750 applies tension, or relieves tension depending on the direction of axial movement of deflection control knob 750, to control the deflection of the distal articulatable sheath relative to the proximal filter and proximal sheath 744, which has been described herein. Rotation of distal sheath actuator 746 will rotate the distal sheath relative to the proximal filter and proximal sheath. The handle also includes housing 740, in which proximal sheath hub 742 is disposed. Proximal sheath hub 742 is secured to proximal sheath 744 and is adapted to be moved axially to control the axial movement of proximal sheath 744.

Figure 35:
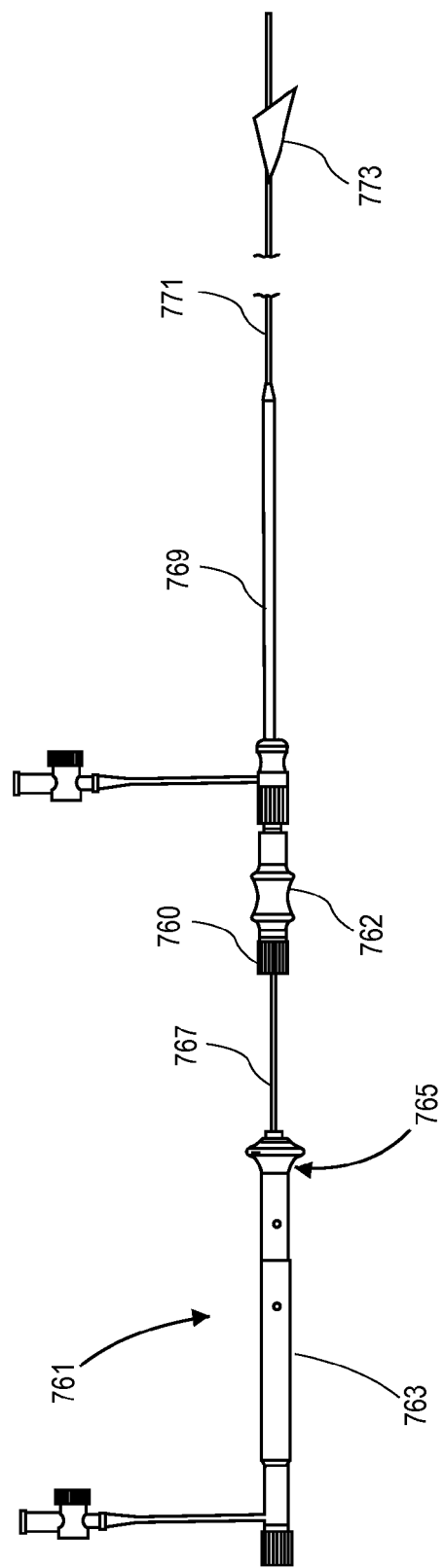

FIG. 35 illustrates another exemplary embodiment of a handle that can be used with any of the filter systems described herein. In this alternate embodiment the handle is of a 3-piece design. This 3-piece handle design comprises a first proximal piece which includes distal sheath actuator 761, which includes handle section 763 and deflection control knob 765. Deflection control knob 765 of distal sheath actuator 761 is secured to distal shaft 767. Axial movement of distal sheath actuator 761 will translate distal shaft 767 either distally or proximally relative to the proximal filter and proximal sheath. A pull wire (not shown in FIG. 35) is secured to handle section 763 and to the distal articulatable sheath (not shown in FIG. 35). Axial movement of deflection control knob 765 applies tension, or relieves tension depending on the direction of axial movement of deflection control knob 765, to control the deflection of the distal articulatable sheath relative to the proximal filter and proximal sheath 769. Rotation of distal sheath actuator 761 will rotate the distal sheath relative to the proximal filter and proximal sheath 769. The handle design further includes a second piece comprising central section 760 which is secured to proximal shaft 771. A third distal piece of this handle design includes housing 762. Housing 762 is secured to proximal sheath 769. Housing 762 is adapted to move axially with respect to central section 760. With central section 760 held fixed in position, axial movement of housing 762 translates to axial movement of proximal sheath 769 relative to proximal shaft 771. In this manner, proximal filter 773 is either released from the confines of proximal sheath 769 into expandable engagement within the vessel or, depending on direction of movement of housing 762, is collapsed back into proximal sheath 769.

While specific embodiments have been described herein, it will be obvious to those skilled in the art that such embodiments are provided by way of example only. Numerous variations, changes, and substitutions will now occur to those skilled in the art without departing from that which is disclosed. It should be understood that various alternatives to the embodiments described herein may be employed in practicing the disclosure.

What is claimed is:

1. An intravascular blood filter system, comprising:
    an expandable proximal filter adapted to be collapsed within a proximal sheath;
    a distal articulatable sheath disposed distal to the proximal sheath, the distal articulatable sheath comprising a first proximal articulatable section, a second distal articulatable section, and a lumen extending through the first proximal articulatable section and the second distal articulatable section, the first proximal articulatable section configured to curve in a first direction and the second distal articulatable section configured to curve in a second direction that is different than the first direction, wherein the first proximal articulatable section comprises a slotted tube and the second distal articulatable section comprises a braided tube;
    a pull wire having a length with a proximal end and a distal section coupled to the distal articulatable sheath, the pull wire crossing from a side of the lumen within the first proximal articulatable section to an opposite side of the lumen within the second distal articulatable section, wherein retraction of the pull wire causes the first proximal articulatable section to curve in the first direction and the second distal articulatable section to curve in the second direction; and
    an expandable distal filter adapted to be collapsed within the distal articulatable sheath, wherein the distal articulatable sheath is adapted to be independently articulated relative to the proximal sheath and the proximal filter, wherein the first proximal articulatable section and the second distal articulatable section are separate constructions with different types of articulable structures.

2. The filter system of claim 1 wherein the proximal sheath is adapted to be proximally retracted relative to the proximal filter to allow the expandable proximal filter to expand from a collapsed configuration within the proximal sheath to an expanded configuration outside of the proximal sheath.

3. The filter system of claim 2 wherein the proximal filter is secured to a proximal shaft disposed within the proximal sheath, and wherein the proximal sheath is adapted to be proximally retracted relative to the proximal shaft.

4. The filter system of claim 1 wherein the distal articulatable sheath is adapted to bend relative to the proximal sheath and the proximal filter.

5. The filter system of claim 4 wherein the distal articulatable sheath has a preset bent configuration.

6. The filter system of claim 1 wherein the distal articulatable sheath is adapted to be axially translated relative to the proximal sheath and the proximal filter.

7. The filter system of claim 1 wherein the distal articulatable sheath is adapted to be rotated relative to the proximal sheath and the proximal filter.

8. The filter system of claim 1 wherein the distal articulatable sheath is adapted to be bent, to be axially translated, and to be rotated, relative to the proximal sheath and the proximal filter.

9. The filter system of claim 1 further comprising a guiding member carrying the distal filter.

10. The system of claim 9 wherein the guiding member is adapted to be moved distally relative to the distal sheath to expand the distal filter from a collapsed configuration within the distal sheath to an expanded configuration outside of the distal sheath.

11. The system of claim 9 wherein the distal sheath is secured to a distal shaft, and wherein the guiding member is disposed with the distal shaft and adapted to be axially movable relative to the distal shaft.

12. The system of claim 11 wherein the distal shaft is co-axial with the proximal sheath.

13. The filter system of claim 1, wherein the proximal filter is secured to a proximal shaft disposed radially within the proximal sheath, wherein the distal sheath is secured to a distal shaft, wherein the distal filter is carried by a guiding member, and wherein the proximal sheath is adapted to be axially moved relative to the proximal filter, the distal sheath, and the distal filter, and wherein the distal filter is adapted to be independently axially moved relative to the proximal sheath, proximal filter, and the distal sheath.

14. The filter system of claim 1 wherein the distal and proximal sheaths have substantially the same outer diameter.

15. The filter system of claim 1 wherein the distal articulatable sheath is configured with a preset S-bend configuration.

16. An intravascular blood filter system, comprising:
a proximal sheath;
a proximal shaft extending through proximal sheath,
an expandable proximal filter carried by the proximal shaft collapsed within the proximal sheath;
a distal shaft extending through the proximal shaft and the expandable proximal filter;
a distal articulatable sheath carried by the distal shaft and positioned distal to a distal end of the proximal sheath and the expandable proximal filter;
a guiding member extending through the distal articulatable sheath;
an expandable distal filter carried by the guiding member and collapsed within the distal articulatable sheath and distal to the distal end of the proximal sheath;
wherein the proximal sheath and the proximal filter allow relative axial translation to allow the proximal filter to expand from a collapsed configuration within the proximal sheath to an expanded configuration outside of the proximal sheath as the proximal sheath is withdrawn with respect to the proximal filter, and
wherein the guiding member and the distal sheath allow for relative axial translation to allow the expandable distal filter to expand from a collapsed configuration within the distal articulatable sheath to an expanded configuration outside of the distal articulatable sheath as the guiding member and the expandable distal filter is advanced with respect to the distal sheath;
wherein the distal articulatable sheath comprises a first proximal articulatable section, a second distal articulatable section, and a lumen extending through the first proximal articulatable section and the second distal articulatable section, the first proximal articulatable section comprising an articulable hypotube with a plurality of slots formed therein and the second distal articulatable section not including a hypotube with a plurality of slots formed therein and a pull wire having a length with a proximal end and a distal section coupled to the distal articulatable sheath, the pull wire crossing from a side of the lumen within the first proximal articulatable section to an opposite side of the lumen within the second distal articulatable section, wherein retraction of the pull wire causes the first proximal articulatable section and the second distal articulatable section to curve, wherein the first proximal articulatable section comprises a slotted tube and the second distal articulatable section comprises a braided tube.

17. The filter system of claim 16 wherein the proximal filter is secured to the proximal shaft radially disposed within the proximal sheath.

18. The filter system of claim 16 wherein the distal articulatable sheath has a preset S-bend configuration.

19. An intravascular blood filter system comprising:
a handle;
a proximal shaft secured to the handle;
a proximal sheath secured to the handle and axially movable with respect to the proximal shaft; a proximal filter secured to the proximal shaft, wherein the proximal sheath is axially movable with respect to the proximal filter;
a distal shaft secured to the handle;
a distal articulatable sheath secured to the distal shaft and axially movable with respect to the proximal sheath, the distal articulatable sheath comprising a first proximal articulatable section, a second distal articulatable section, and a lumen extending through the first proximal articulatable section and the second distal articulatable section, the first proximal articulatable section configured to curve in a first direction and the second distal articulatable section configured to curve in a second direction that is different than the first direction, wherein the first proximal articulatable section comprises a first type of articulable structure and the second distal articulatable section comprises a separate type of articulable structure that is different from the first type of articulable structure, wherein the first proximal articulatable section comprises a slotted tube and the second distal articulatable section comprises a braided tube;
a distal filter shaft;
a distal filter secured to the distal filter shaft and axially movable with respect to the proximal sheath and the distal articulatable sheath; and
a single actuation member extending between the handle and the distal articulatable sheath wherein actuation of the single actuation member causes the first proximal articulatable section to curve in the first direction and the second distal articulatable section to curve in the second direction, the single actuation member crossing from a side of the lumen within the first proximal articulatable section to an opposite side of the lumen within the second distal articulatable section.

20. The intravascular blood filter system of claim 19 wherein the single actuation member comprises:
   a pull wire having a length with a proximal end and a distal section; and
   wherein the pull wire proximal end is secured to the handle and the pull wire distal section is secured to the distal articulatable sheath.

21. The intravascular blood filter system of claim 19 wherein the handle comprises a first handle section secured to the proximal sheath and a second handle section secured to the distal shaft.

22. The intravascular blood filter system of claim 21 wherein the first handle section houses a proximal hub secured to the proximal sheath, and wherein the proximal hub is adapted to be slideable within the first handle section to cause axial movement of the proximal sheath.

23. The intravascular blood filter system of claim 21 wherein the second handle section further comprises a deflection knob which is adapted to be slideable within and movable with respect to the second handle section.

24. The intravascular blood filter system of claim 23 wherein the single actuation member comprises:
   a pull wire having a length with a proximal end and a distal section;
   wherein the pull wire proximal end is secured to the second handle section and the pull wire distal section is secured to the distal articulatable sheath;
   wherein the distal shaft is secured to the deflection knob; and
   whereby movement of either the deflection knob or the second handle section relative to and in a direction away from each other tensions the pull wire thereby causing deflection of the distal articulatable sheath.

25. The intravascular blood filter system of claim 19 wherein the handle comprises a first handle section secured to the proximal sheath, a second handle section secured to the proximal shaft, and a third handle section secured to the distal shaft.

26. The intravascular blood filter system of claim 25 wherein the second handle section is disposed between the first handle section and the third handle section and wherein the first and third handle sections are movable relative to each other and relative to the second handle section.

27. The intravascular blood filter system of claim 26 wherein the single actuation member comprises: a pull wire having a length with a proximal end and a distal section; wherein the pull wire proximal end is secured to the third handle section and the pull wire distal section is secured to the distal articulatable sheath.

28. The intravascular blood filter system of claim 27 wherein:
   the third handle section further comprises a deflection knob which is slideable within and movable with respect to the third handle section;
   wherein the pull wire is secured to the third handle section;
   wherein the distal shaft is secured to the deflection knob; and
   whereby movement of either the deflection knob or the third handle section relative to and in a direction away from each other tensions the pull wire thereby causing deflection of the distal articulatable sheath.

29. The intravascular blood filter system of claim 19 wherein the slotted tube is metal.

30. The intravascular blood filter system of claim 29 wherein the slotted tube is comprised of a plurality of transverse slots.

31. The intravascular blood filter system of claim 19 wherein the single actuation member comprises:
   a pull wire having a length with a proximal end and a distal section;
   wherein the pull wire proximal end is secured to the handle and the pull wire distal section is secured to the first proximal articulatable section of the distal articulatable sheath and the second distal articulatable section of the distal articulatable sheath;
   wherein the handle is configured such that movement of the handle tensions or relieves tension on the pull wire; and
   whereby initial tensioning of the pull wire causes the first proximal articulatable section to deflect in a first direction having a first radius of curvature and further tensioning of the pull wire causes the second distal articulatable section to deflect in a second direction with a second radius of curvature.

32. The intravascular blood filter system of claim 31 wherein the distal articulatable sheath is adapted to be articulated into a configuration substantially similar to a shepherd's staff or crook.

33. The intravascular blood filter system of claim 19 wherein the proximal filter is expandable and adapted to be collapsed within the proximal sheath.

34. The intravascular blood filter system of claim 33 wherein the proximal filter is configured as an oblique truncated cone.

35. The intravascular blood filter system of claim 34 wherein the proximal filter comprises an expandable frame comprising a stiffening element extending at least partially along the length of the proximal filter.

36. The intravascular blood filter system of claim 33 wherein the proximal filter comprises an oblique truncated conical filter with an expandable frame and a stiffening element extending along a length thereof from a point proximate the proximal shaft to a point proximate the shorter length of the oblique truncated conical filter.

37. The intravascular blood filter system of claim 19 wherein the proximal filter has a plurality of holes formed therein to allow blood to be filtered therethrough.

38. The intravascular blood filter system of claim 37 wherein the plurality of holes are triangular in shape.

39. An intravascular blood filter system comprising:
   a handle comprising a first handle section and a second handle section; a proximal shaft secured to the first handle section;
   a proximal sheath secured to the first handle section and axially movable with respect to the proximal shaft;
   an expandable proximal filter secured to the proximal shaft and collapsible within the proximal sheath and wherein the proximal sheath is axially movable with respect to the proximal filter;
   a distal shaft secured to the second handle section;
   a distal articulatable sheath secured to the distal shaft and axially movable with respect to the proximal sheath wherein the distal articulatable sheath comprises a first proximal articulatable section, a second distal articulatable section, and a lumen extending through the first proximal articulatable section and the second distal articulatable section, wherein the first proximal articulatable section comprises a first type of articulable structure where bending is limited and the second distal articulatable section comprises a separate type of articulable structure where the bending is not limited, wherein the first proximal articulatable section comprises a slotted tube and the second distal articulatable section comprises a braided tube;

a pull wire having a length with a proximal end and a distal section wherein the pull wire proximal end is secured to the second handle section and the pull wire distal section is secured to the distal articulatable sheath, the pull wire crossing from a side of the lumen within the first proximal articulatable section to an opposite side of the lumen within the second distal articulatable section, wherein retraction of the pull wire causes the first proximal articulatable section to curve in a first direction and the second distal articulatable section to curve in a second different direction;

a distal filter shaft; and an expandable distal filter secured to the distal filter shaft and collapsible within the distal shaft and distal articulatable sheath and wherein the distal filter is axially movable with respect to the proximal sheath, the distal shaft and the distal articulatable sheath.

40. The filter system of claim 1 wherein retraction of the pull wire causes the first proximal articulatable section to bend out of plane.

41. The filter system of claim 1 wherein retraction of the pull wire causes the second distal articulatable section to continue to curve in the second different direction after the first proximal articulatable section has stopped bending.

42. The filter system of claim 41 wherein the first proximal articular section stops bending as slots in the first proximal articulatable section narrow and touch one another.

43. The intravascular blood filter system of claim 19 wherein actuation of the single actuation member causes the first proximal articulatable section to bend out of plane.

44. The intravascular blood filter system of claim 19 wherein actuation of the single actuation member causes the second distal articulatable section to continue to curve in the second different direction after the first proximal articulatable section has stopped bending.

45. The intravascular blood filter system of claim 44 wherein the first proximal articulatable section stops bending as slots in the first proximal articulatable section narrow and touch one another.

46. The intravascular blood filter system of claim 39 wherein retraction of the pull wire causes the first proximal articulatable section to bend out of plane.

47. The intravascular blood filter system of claim 39 wherein retraction of the pull wire causes the second distal articulatable section to continue to curve in the second different direction after the first proximal articulatable section has stopped bending.

48. The intravascular blood filter system of claim 47 wherein the first proximal articulatable section stops bending as slots in the first proximal articulatable section narrow and touch one another.

* * * * *